(12) United States Patent
Balduini et al.

(10) Patent No.: US 11,802,270 B2
(45) Date of Patent: Oct. 31, 2023

(54) MICROPHYSIOLOGIC METHODS AND COMPOSITIONS

(71) Applicants: Tufts University, Medford, MA (US); University of Pavia, Pavia (IT)

(72) Inventors: Alessandra Balduini, Pavia (IT); David L. Kaplan, Concord, MA (US); Lindsay Wray, Fairfield, CA (US); Christian Andrea Di Buduo, Pavia (IT); Lorenzo Tozzi, Pavia (IT)

(73) Assignees: Tufts University, Medford, MA (US); University of Pavia, Pavia (IT)

( * ) Notice: Subject to any disclaimer, the term of this patent is extended or adjusted under 35 U.S.C. 154(b) by 92 days.

(21) Appl. No.: 15/501,607

(22) PCT Filed: Aug. 6, 2015

(86) PCT No.: PCT/US2015/044066
§ 371 (c)(1),
(2) Date: Feb. 3, 2017

(87) PCT Pub. No.: WO2016/022834
PCT Pub. Date: Feb. 11, 2016

(65) Prior Publication Data
US 2017/0218339 A1    Aug. 3, 2017

Related U.S. Application Data

(60) Provisional application No. 62/034,727, filed on Aug. 7, 2014.

(51) Int. Cl.
*C12N 5/078*    (2010.01)

(52) U.S. Cl.
CPC ........ *C12N 5/0644* (2013.01); *C12N 2502/28* (2013.01); *C12N 2533/50* (2013.01)

(58) Field of Classification Search
CPC .............. C12N 5/0644; C12N 2502/28; C12N 2533/50
See application file for complete search history.

(56) References Cited

U.S. PATENT DOCUMENTS

2012/0238020 A1    9/2012   Mitchell et al.

FOREIGN PATENT DOCUMENTS

| CN | 1260363 A | 7/2000 | |
|----|-----------|--------|---|
| WO | WO-2013070907 A1 * | 5/2013 | ............. A61L 27/36 |

(Continued)

OTHER PUBLICATIONS

Isabella Pallotta, Michael Lovett, David L. Kaplan and Alessandra Balduini, Three-Dimensional System for the In Vitro Study of Megakaryocytes and Functional Platelet Production Using Silk-Based Vascular Tubes, 2011, Tissue Engineering: Part C, vol. 17, No. 12, pp. 1223-1232 (Year: 2011).*

(Continued)

*Primary Examiner* — David W Berke-Schlessel
*Assistant Examiner* — Trent R Clarke
(74) *Attorney, Agent, or Firm* — GTC Law Group PC & Affiliates

(57) ABSTRACT

The present invention provides, among other things, methods for producing platelets including the steps of providing a silk membrane about 2 μm and 100 μm thick, inclusive, contacting the silk membrane with a porogen to form a porous silk membrane comprising at least one silk wall defining a lumen, associating the porous silk membrane with stromal derived factor-1? and at least one functionalizing agent, forming a three dimensional silk matrix comprising interconnected pores wherein the pores have a diameter of between about 5 and 500 μm, inclusive, wherein the silk matrix is formed around at least a portion of the porous silk membrane, introducing a plurality of megakaryocytes to the (Continued)

silk matrix such that the megakaryocytes are located at least partially within the porous silk matrix, and stimulating the plurality of megakaryocytes to produce platelets. Also provided are various new compositions and methods of making those compositions.

23 Claims, 16 Drawing Sheets

(56) References Cited

FOREIGN PATENT DOCUMENTS

| WO | WO-2013/119551 A1 | 8/2013 |
| WO | WO-2014/012105 A1 | 1/2014 |
| WO | WO-2014/100779 A1 | 6/2014 |

OTHER PUBLICATIONS

International Search Report for PCT/US2015/044066, 3 pages (dated Nov. 4, 2015).
Written Opinion for PCT/US2015/044066, 5 pages (dated Nov. 4, 2015).

* cited by examiner

MICROPHYSIOLOGIC METHODS AND COMPOSITIONS

CROSS REFERENCE TO RELATED APPLICATIONS

This application is a U.S. National Stage Application filed under 35 U.S.C. § 371 based on International Application No. PCT/US2015/044066, filed Aug. 6, 2015, which claims priority to U.S. Provisional application No. 62/034,727, Aug. 7, 2014, the entire contents of each of which are hereby incorporated herein by reference.

GOVERNMENT SUPPORT

This invention was made with government support under grant EB016041 awarded by the National Institutes of Health. The government has certain rights in the invention.

BACKGROUND

About 16 million blood donations are collected annually in U.S.A. and 1.5 million platelet concentrates are transfused in the U.S.A. each year at a cost of about $900 million dollars. Generally, platelet concentrates are needed by people who lack platelets or whose platelets function improperly, such as certain cancer chemotherapy, bone marrow transplant patients, trauma patients given massive blood transfusion and people with aplastic anemia. The concentrates from volunteer donors are expensive to make, require 10 or more tests for pathogens and have a shelf life of only five days. As a result, 20 to 40 percent of platelets concentrates are discarded.

Currently, platelets are collected either from donated blood or by apheresis. The short shelf life means platelets cannot easily be shipped from an area of surplus to one of scarcity, and hospitals occasionally experience shortages that require surgeries to be postponed. Additionally, platelet transfusions expose patients to risks of disease transmission and can induce acute reactions and alloimmunization that makes patients refractory to subsequent platelet infusions. With such widespread impact of these diseases, and the lack of good options for clinical treatments, new insight into the formation of platelets would have a major impact on patients and healthcare.

SUMMARY

The present invention provides, inter alia, new methods and compositions for the production of human platelets. In contrast to previously available methods, provided methods and compositions, in some embodiments, provide highly customizable models of human bone marrow characterized at least in part by their ability to produce differentiated, functional platelets in vitro at numbers at least an order of magnitude above that achieved by previously known solutions. For instance, the present invention provides methods and compositions for the production of about $0.8 \times 10^6$ to about $2.0 \times 10^6$ differentiated and functional platelets in about 6 hours whereas previously available methods, which also utilized silk tubes, produced only 200+/−50 per megakaryocyte that extended proplatelets in 16 hours (Pallotta et al. Tissue Engineering (2011) 17:1223-1232).

In some embodiments, the present invention provides compositions including a porous silk membrane between about 2-100 µm thick, inclusive, comprising at least one silk wall defining a lumen, at least one functionalizing agent, stromal derived factor-1α, and a three dimensional silk matrix comprising interconnected pores wherein the pores have a diameter of between about 5 and 500 µm, inclusive, wherein the three dimensional silk matrix at least partially surrounds the silk membrane, and wherein the stromal derived factor-1α is associated with the silk membrane.

In some embodiments, the present invention provides methods of forming a bioreactor including the steps of providing a silk membrane about 2-100 µm thick, inclusive, contacting the silk membrane with a porogen to form a porous silk membrane comprising at least one silk wall defining a lumen, associating the porous silk membrane with stromal derived factor-1α and at least one functionalizing agent, forming a three dimensional silk matrix comprising interconnected pores wherein the pores have a diameter of between about 5 and 500 µm, inclusive, and wherein the silk matrix is formed around at least a portion of the porous silk membrane.

In some embodiments, the present invention provides methods of producing platelets including the steps of providing a silk membrane about 2 µm and 100 µm thick, inclusive, contacting the silk membrane with a porogen to form a porous silk membrane comprising at least one silk wall defining a lumen, associating the porous silk membrane with stromal derived factor-1α and at least one functionalizing agent, forming a three dimensional silk matrix comprising interconnected pores wherein the pores have a diameter of between about 5 and 500 µm, inclusive, wherein the silk matrix is formed around at least a portion of the porous silk membrane, introducing a plurality of megakaryocytes to the silk matrix such that the megakaryocytes are located at least partially within the porous silk matrix, and stimulating the plurality of megakaryocytes to produce platelets.

In some embodiments, the associating step comprises immobilizing at least a portion of the stromal derived factor-1α and/or at least one functionalizing agent within the porous silk membrane. In some embodiments, the associating step comprises adsorbing at least a portion of the stromal derived factor-1α and/or at least one functionalizing agent onto a surface of the porous silk membrane.

Any of a variety of porogens may be used in accordance with various embodiments. In some embodiments, a porogen is polyethylene oxide (PEO). In some embodiments, a porogen is a laser.

According to various embodiments, a variety of functionalizing agents may be used. In some embodiments, the at least one functionalizing agent is an extracellular matrix protein. In some embodiments, the extracellular matrix protein is selected from fibronectin, collagen type I, collagen type IV, collagen type VI, vitronectin, proteoglycans, decorin, hyaluronan, von Willebrand factor, laminin, fibrinogen and/or other extracellular matrix components.

In some embodiments, provided methods and compositions further comprise a plurality of endothelial cells located at least partially within the lumen. In some embodiments, the endothelial cells are selected from: human dermal microvascular endothelial cells, human umbilical vein endothelial cells, and primary human endothelial cells. In some embodiments, the endothelial cells form a confluent layer. In some embodiments, the confluent layer of endothelial cells exhibit a cobblestone morphology. In some embodiments the confluent layer of endothelial cells exhibit VE-cadherin staining.

In some embodiments, provided methods and compositions further comprise a plurality of megakaryocytes located at least partially within the three dimensional silk matrix. One exemplary advantage provided by some embodiments is production of a high proportion of differentiated and/or functional platelets. In some embodiments, the megakaryocytes produce platelets in the lumen. In some embodiments, at least 70% of the platelets produced express CD61. In some embodiments, platelets produced exhibit a similar morphology and CD41 positive staining as compared to platelets isolated form peripheral blood. In some embodiments, about 30 to 3000 fold more platelets are produced per seeded cell when in the presence of endothelial cells as compared to a seeded cell not in the presence of endothelial cells. In some embodiments, platelets produced bind PAC-1. In some embodiments, platelets produced bind PAC-1 following stimulation with thrombin, ADP and/or epinephrine. In some embodiments, platelets produced express CD61 and/or CD42b.

In some embodiments, provided compositions further comprise culture media flowing through the composition at a flow rate of about 20 µL/minute to 250 µL/minute. In some embodiments, the composition is characterized as being able to produce about $0.8 \times 10^6$ to about $2.0 \times 10^6$ platelets in about 6 hours. In some embodiments, the composition is characterized as being able to produce about $0.13 \times 10^6$ to about $0.33 \times 10^6$ platelets per hour.

In some embodiments, the provided methods of forming a bioreactor further comprise introducing culture media at a flow rate of about 20 µL/minute to 250 µL/minute to the bioreactor. In some embodiments, the culture media flows through the bioreactor at a flow rate of about 32 µL/minute for about 24 hours and the platelets are collected. In some embodiments, the culture media flows through the bioreactor at a flow rate of about 94 µL/minute for about 6 hours and the platelets are collected. In some embodiments, about $0.8 \times 10^6$ to about $2.0 \times 10^6$ platelets are produced in about 6 hours. In some embodiments, about $0.13 \times 10^6$ to about $0.33 \times 10^6$ platelets are produced per hour. In some embodiments, about 100-fold more platelets are produced from the bioreactor as compared to the same bioreactor without the confluent layer of endothelial cells in the same amount of time.

In some embodiments, the provided methods of producing platelets further comprise introducing culture media at a flow rate of about 20 µL/minute to 250 µL/minute to at least one of the silk matrix and silk membrane. In some embodiments, wherein the culture media flows through at least one of the silk matrix and silk membrane at a flow rate of about 32 µL/minute for about 24 hours and the platelets are collected. In some embodiments, the culture media flows through at least one of the silk matrix and silk membrane at a flow rate of about 94 µL/minute for about 6 hours and the platelets are collected. In some embodiments, about $0.8 \times 10^6$ to about $2.0 \times 10^6$ platelets are produced in about 6 hours. In some embodiments, about $0.13 \times 10^6$ to about $0.33 \times 10^6$ platelets are produced per hour.

According to various embodiments, a porous silk membrane may be formed into any of a variety of shapes. In some embodiments, a porous silk membrane is a sheet (for example, a film), a tube, a sphere or portion thereof or other application-appropriate shape.

Various embodiments may comprise three dimensional silk membranes comprising pores of various sizes. In some embodiments, pores in a three dimensional silk membrane have a diameter between about 5-10 µm, inclusive.

Provided silk membranes may be of a variety of different thicknesses. In some embodiments, a porous silk membrane is about 50-70 µm thick, inclusive. In some embodiments, a silk membrane is of a substantially uniform thickness. In some embodiments, a silk membrane varies in thickness across a silk wall.

Various embodiments may comprise a silk matrix with pores of any of a variety of sizes. In some embodiments the pores of the three dimensional silk matrix have a diameter of between about 300 and 500 µm, inclusive.

Any of a variety of methods may be used to make a silk membrane according to various embodiments. In some embodiments, a silk membrane is made via gel spinning.

In some embodiments, the present invention provides methods of producing platelets comprising activating a system, the system comprising megakaryocytes, wherein at least about $0.8 \times 10^6$ to about $2.0 \times 10^6$ platelets are produced by the system in 6 hours. In some embodiments, about $0.13 \times 10^6$ to about $0.33 \times 10^6$ platelets are produced per hour.

As used in this application, the terms "about" and "approximately" are used as equivalents. Also, the terms "composition" and "bioreactor" are used as equivalents. Any numerals used in this application with or without about/ approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

Figure 1:
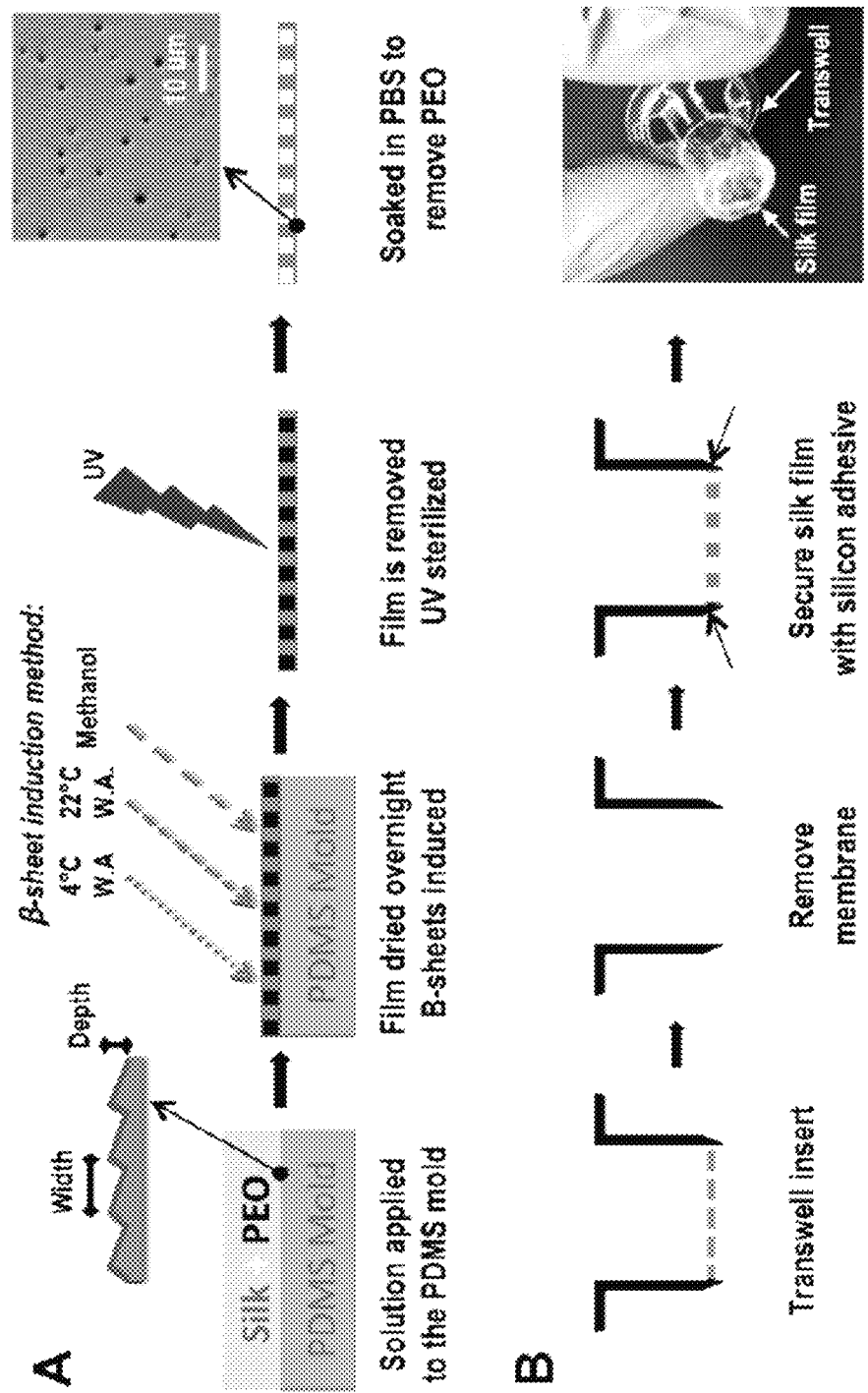
FIG. 1A-B show flow diagrams of exemplary provided methods. Panel A shows an exemplary method wherein silk films are made and panel B shows an exemplary method of using such films to assemble a culture system assembly.

Silk films are prepared by dispensing a silk and polyethylene oxide (PEO) solution onto a polydimethylsiloxane (PDMS) mold. The surface of the mold may contain a grating pattern with defined depth and width. When the solution dries, a silk film is formed that contains a dispersion of PEO porogens. The film is finally soaked in PBS to remove the PEO porogen. (B) Representative confocal microscopy image of silk film porosity (scale bar=25 µm). (C-D) Analysis of Mk adhesion and proplatelet formation on silk film with different topography coated with fibrinogen (average±SD, n=3, p=NS). Results are presented relative to silk film with no pattern. (E) AFM elastic modulus values obtained over hydrated Low, Medium, and High films. Distributions are displayed as percent of total sample points measured per bin. All samples have a minimum of 300 measurements. (F) There was no significant difference in Mk adhesion between the different stiffness samples (average±SD, n=4, p=NS). (G) The low stiffness samples had similar proplatelet formation compared to the medium stiffness, but significantly higher percentage compared to the high stiffness samples (average±SD, n=4, *p<0.01). (H) Representative fluorescent images of Mk cultures on silk films with different stiffness after 16 hours incubation. The low stiffness silk films supported long proplatelet extensions and increased silk film stiffness appeared to decreased proplatelet branching (red=β1-tubulin, blue=nuclei, scale bar=50 µm).

FIG. 11A-F. Effect of silk film functionalization on megakaryocyte adhesion and proplatelet formation. (A-B) Mk adhesion and proplatelet formation on functionalized silk films follows a similar trend compared to coated glass cover-slips or silk film (error bars=SD, n=4). (C) Representative fluorescent images of Mk cultured on coated glass cover slips, coated silk films or entrapped silk films. Mks were able to sense the proteins entrapped in silk films as they normally spread on type I collagen (COLI) and form proplatelet on fibrinogen (FBG) in all tested conditions (green=α-tubulin, blue=nuclei, scale bar=50 µm). (D-E) We also analyzed effect of silk films functionalization with bone marrow vascular niche ECM components: fibronectin (FNC), type IV collagen (COL IV), laminin (LAM). Both Mk adhesion and proplatelet formation were not different between the three tested ECM components, but significantly higher compared to an unfunctionalized silk film control (average±SD, n=3, *p<0.05). (F) Representative fluorescent images of Mks cultured for 16 hours on functionalized silk films show that proplatelet morphology is almost similar between the three tested conditions (green=β1-tubulin, blue=nuclei, scale bar=50 µm).

FIG. 12A-D. Co-culture of Mks and EPCs in the silk film culture system. (A) Schematic of the EPC and Mk seeding procedure for establishment of the silk film model. (B) After 16 hours of culture on the basal side of the silk film membrane, EPCs exhibit the characteristic cobblestone morphology and expression of VE-cadherin on both glass coverslip control (B I) and functionalized silk film (B II) (green=VE-cadherin, blue=nuclei, scale bar=100 µm). (B III-IV) Representative fluorescent image of Mk and EPC co-culture on the silk film culture system (green=VE-Cadherin, red=CD61, blue=nuclei, scale bar=50 µm). (V-VI) Representative cross-section image of Mk and EPC co-culture rendered using confocal microscopy. There is distinct localization of the EPCs (green) on the basal side of the membrane and Mks (red) on the upper side of the membrane (green=VE-Cadherin, red=CD61, blue=nuclear, scale bar=20 µm). Silk films were stained with Hoechst 33258 and visualized in blue. (C) $CD61^+CD42b^+$ peripheral blood platelets were used to set the platelet gating protocol. In vitro produced platelets showed similar staining and physical parameters of peripheral blood platelets. (D) Mks cultured on functionalized silk films in presence of EPCs produced a significantly increased number of platelets compared to functionalized silk films only (average±SD, n=3, *p<0.05).

Figure 13:
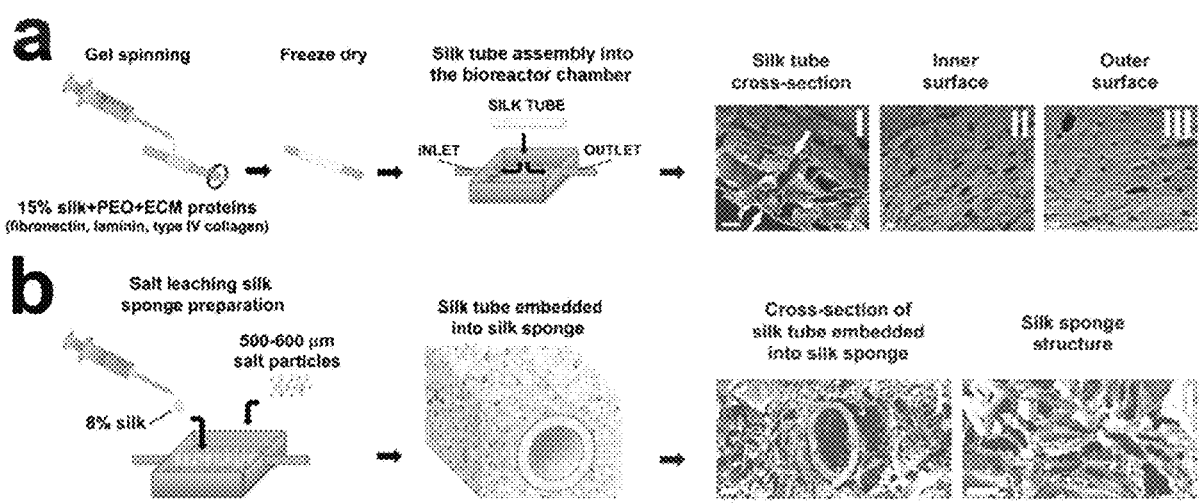

FIG. 13A-B. Silk microtube and sponge preparation and assembly into the bioreactor chamber. (A) Silk tubes were prepared by gel spinning aqueous silk solutions containing a polyethylene oxide (PEO) porogen around a wire and functionalized via entrapment of extracellular matrix (ECM) components. The gel spun-silk was freeze-dried, removed from the wire and soaked in water to leach out the PEO porogen. The resulting porous silk microtubes were fitted into the bioreactor chamber. (A I) SEM cross sections of a silk microtube: microtube wall thickness was 50±20 µm with microtube wall pores diameter of 22±4 µm to allow proplatelet elongation (scale bar=20 µm). Arrows indicate silk microtubes borders. (A II and III) SEM images show pores on both the inner and outer surfaces of the silk microtubes, respectively. The inner and outer microtube wall pores diameter was 6±2 µm (scale bars=20 µm). (B) Aqueous silk was dispensed into the chamber around the microtube and salt particle porogens were added. After leaching out the salt porogens, the resulting porous silk sponge was trimmed and sterilized. (B I) SEM image shows a silk microtube embedded into the silk sponge (scale bar=100 µm). (B II) SEM image shows the porous morphology of silk sponge (scale bar=100 µm).

Figure 14:
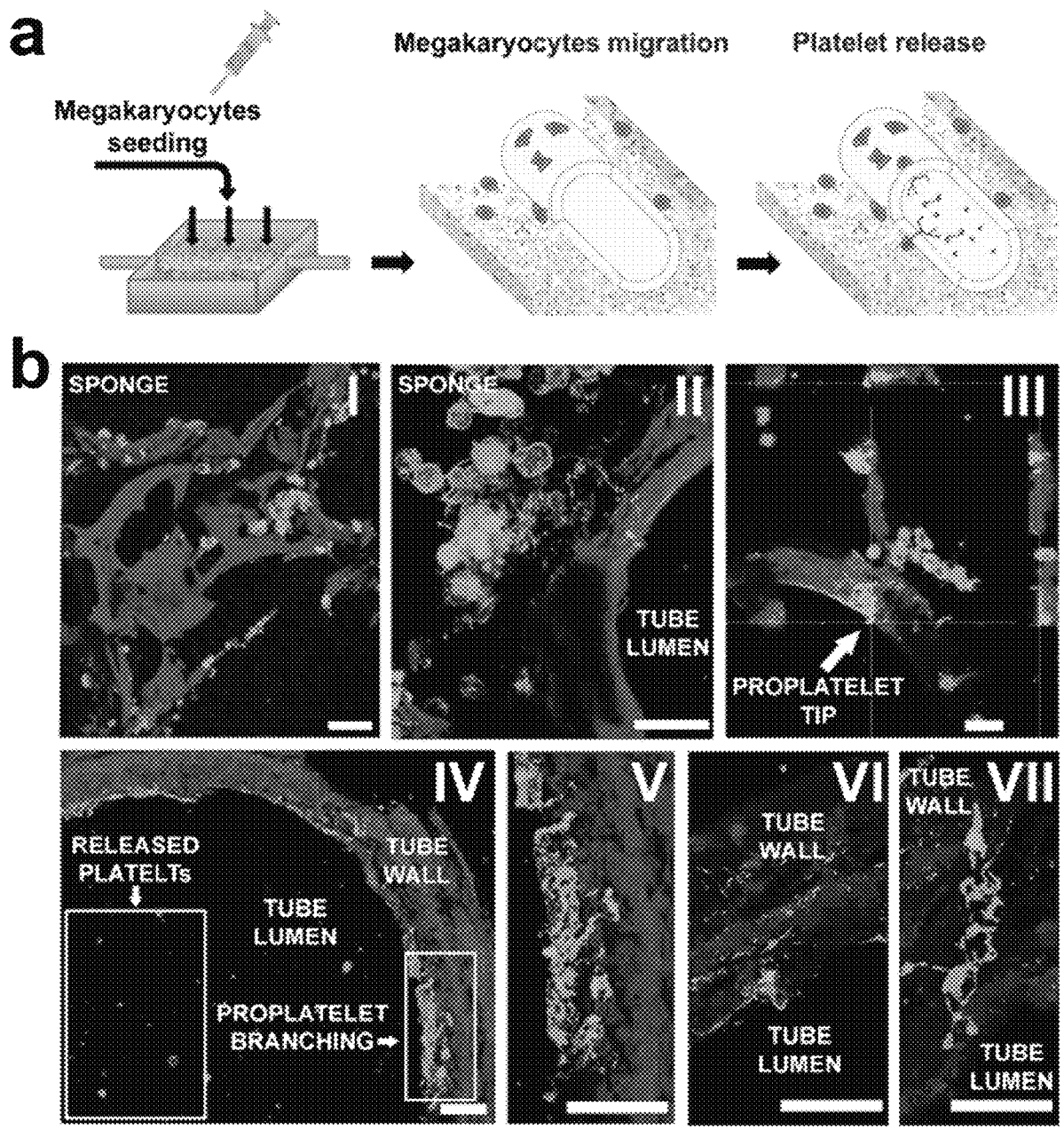

FIG. 14A-B. Proplatelet formation and platelet production within the silk microtube-sponge construct. (A) After seeding into the silk sponge Mks migrate towards the microtube, adhere and extend proplatelets through the microtube wall to release platelets into the microtube lumen. (B I) Confocal microscopy image of mature Mks immediately after seeding into the silk sponge (green=CD61; blue=nuclei; scale bar=100 µm). (B II) During the course of 24 hours, Mks migrated towards the microtube. Confocal microscopy analysis shows Mks in close contact with the microtube wall (green=CD61; blue=nuclei; scale bar=50 µm). (B III) Mks extending proplatelets through the silk microtube wall. Orthogonal projections show proplatelet branches elongation through microtube walls with proplatelet tips protruding into the microtube lumen (green=CD61; blue=nuclei; scale bar=50 µm). (B IV) Boxes highlight proplatelet-forming Mk detectable along the inner wall of the silk microtube and platelets released directly into the microtube lumen (green=CD61; blue=nuclei; scale bar=50 µm). (B V) Magnification of the proplatelet-forming Mk showed in panel B IV (green=CD61; blue=nuclei; scale bar=50 µm). (B VI and VII) Representative images of proplatelet branches through the porous silk microtube wall (green=CD61; blue=nuclei; scale bar=50 µm). Silk fibroin 3D scaffolds were stained with Hoechst 33258 and visualized in blue.

FIG. 15A-E. Analysis of platelets collected into the microtube effluent. (A) Silk microtubes were perfused with culture media for 6 hours after Mk migration and the released platelets were collected into bags. (B) Ex vivo produced platelets were analyzed with the same physical parameters as human peripheral blood platelets. Samples were mixed with counting beads in order to quantify the number of platelets which were identified as $CD61^+CD42b^+$ vents. (C) Platelet release was analyzed after perfusion of an increasing number of bioreactors with a maximum of four different silk microtubes perfused concurrently. The graph shows the absolute number of platelets released per microtube embedded in the silk sponge containing $2.5 \times 10^5$ Mks.

(D) Collected platelets after bioreactor perfusion revealed increased PAC-1 binding after thrombin, ADP and epinephrine stimulation. (E) Aggregation was measured by flow cytometry after stimulation with a cocktail of thrombin, ADP and epinephrine. Platelets were separately labeled with CD31 or CD42b (left and right top, respectively). The bottom panel shows dot plots of the mixed 1:1 platelets, respectively labeled with CD31 or CD42b, before (left) and after (right) platelet aggregation following stimulation with the agonist cocktail. The double-colored population indicates that the bioreactor released platelets had the functionality to aggregate after the perfusion through the silk microtube. At least five independent experiments were performed for each subset.

FIG. 16A-I. Adding complexity to the system: endothelial and red blood cells. (A) The silk microtube lumen supported a confluent monolayer of human dermal microvascular endothelial cells (HMVEC-d). (B I) Confocal microscopy images of confluent HMVEC-d in the silk microtube lumen (green=VE-cadherin; scale bar=100 µM). (B II) Magnification of HMVEC-d seeded into silk microtube lumen (green=VE-cadherin; blue=nuclei; scale bar=50 µM). (C) Statistical analysis of collected platelets after perfusion of endothelialized silk microtube with respect silk microtube without HMVEC-d (*p<0.05). (D) Collected platelets derived from CFSE labeled Mks seeded into bioreactors and perfused displayed positive staining for both CFSE and CD42b by flow cytometry analysis. (E-F) To mimic aspects of blood perfusion within the model tissue system, the silk vascular microtubes were embedded into silk sponges and perfused with a suspension of 5% erythrocytes. (G) Prior to seeding, the Mks were stained with CFSE and the released platelets were analyzed as CFSE and CD42b positive cells. (H) CFSE$^+$CD42b$^+$ platelets were distinguishable from endogenous platelets and red blood cells (RBCs). (I) The fold increase in collected platelets while being perfused with red blood cells was not statistically different compared to the media-only control (p=NS). At least five independent experiments were performed for each subset.

DEFINITIONS

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Animal: As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Approximately: As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Biocompatible: The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Biodegradable: As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Determine: Many methodologies described herein include a step of "determining" Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Hydrophilic: As used herein, the term "hydrophilic" and/or "polar" refers to a tendency to mix with, or dissolve easily in, water.

Hydrophobic: As used herein, the term "hydrophobic" and/or "non-polar", refers to a tendency to repel, not combine with, or an inability to dissolve easily in, water.

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Subject: By "subject" is meant a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. A subject can be a patient, which refers to a human presenting to a medical provider for diagnosis or treatment of a disease. In some embodiments, a subject is an individual to whom therapy is administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

DETAILED DESCRIPTION OF CERTAIN EMBODIMENTS

The present invention provides, among other things, three dimensional bioengineered tissue co-culture perfusion systems that approximate natural bone marrow and a native vascular microenvironment. In some embodiments, provided methods and compositions allow for the ex vivo production of differentiated and functional platelets. As described herein, various provided embodiments overcome several challenges in the art for which there was previously no satisfactory solution.

In some embodiments, the present invention provides compositions including a porous silk membrane between about 2-100 μm thick, inclusive, comprising at least one silk wall defining a lumen, at least one functionalizing agent, stromal derived factor-1a, and a three dimensional silk matrix comprising interconnected pores wherein the pores have a diameter of between about 5 and 500 μm, inclusive, wherein the three dimensional silk matrix at least partially surrounds the silk membrane, and wherein the stromal derived factor-1α is associated with the silk membrane.

In some embodiments, the present invention also provides methods including the steps of providing a silk membrane about 2-100 μm thick, inclusive, contacting the silk membrane with a porogen to form a porous silk membrane comprising at least one silk wall defining a lumen, associating the porous silk membrane with stromal derived factor-1α and at least one functionalizing agent, forming a three dimensional silk matrix comprising interconnected pores wherein the pores have a diameter of between about 5 and 500 μm, inclusive, and wherein the silk matrix is formed around at least a portion of the porous silk membrane.

Silk Membranes

In contrast to other available membrane types, silk membranes provide special and unique benefits to various embodiments. Silk fibroin, derived from *Bombyx mori* silkworm cocoons, is biocompatible, degrades slowly in the body, is readily modified into a variety of formats and generates mechanically robust materials. According to various embodiments, including those used to produce platelets, these properties, in addition to compliance, variable size, low thrombogenicity, and non-toxicity, among others, represent the qualities of an ideal environment which closely approximates a blood vessel and/or bone marrow. Processing methods described herein allow for the manufacture of silk membranes, for example, silk membranes shaped into tubes, of varying inner diameter, porosity, mechanical strength, and diffusivity.

Silk membranes may be produced using any of a variety of silk solutions. Preparation of silk fibroin solutions has been described previously, e.g., in WO 2007/016524, which is incorporated herein by reference in its entirety. The reference describes not only the preparation of aqueous silk fibroin solutions, but also such solutions in conjunction with bioactive agents.

Silk fibroin solutions used in methods and compositions described herein may be obtained from a solution containing a dissolved silkworm silk, such as, for example, from *Bombyx mori*. Alternatively, a silk fibroin solution is obtained from a solution containing a dissolved spider silk, such as, for example, from *Nephila clavipes*. Silk fibroin solutions can also be obtained from a solution containing a genetically engineered silk. Genetically engineered silk can, for example, comprise a therapeutic agent, e.g., a fusion protein with a cytokine, an enzyme, or any number of hormones or peptide-based drugs, antimicrobials and related substrates.

Provided silk compositions described herein, and methods of making and/or using them may be performed in the absence of any organic solvent. Thus, in some embodiments, provided compositions and methods are particularly amenable to the incorporation of labile molecules, such as bioactive agents or therapeutics, and can, in certain embodiments, be used to produce controlled release biomaterials. In some embodiments, such methods are performed in water only.

As used herein, the term "fibroin" includes, but is not limited to, silkworm fibroin and insect or spider silk protein.

In some embodiments, fibroin is obtained from a solution containing a dissolved silkworm silk or spider silk. In some embodiments silkworm silk protein is obtained, for example, from *Bombyx mori*, and spider silk is obtained from *Nephila clavipes*. In some embodiments, silk proteins suitable for use in the present invention may be obtained from a solution containing a genetically engineered silk, such as from bacteria, yeast, mammalian cells, transgenic animals or transgenic plants. See, for example, WO 97/08315 and U.S. Pat. No. 5,245,012.

A silk fibroin solution can be prepared by any conventional method known to one skilled in the art. According to various embodiments, the solution is an aqueous solution. By way of non-limiting example, *B. mori* cocoons are boiled for about 30 minutes in an aqueous solution. In some embodiments, the aqueous solution is about 0.02M $Na_2CO_3$, and cocoons are rinsed, for example, with water to extract the sericin proteins and the extracted silk is then dissolved in an aqueous salt solution. Exemplary salts useful for this purpose include, but are not limited to, lithium bromide, lithium thiocyanate, calcium nitrate, and/or other chemicals capable of solubilizing silk. In some embodiments, extracted silk is dissolved in about 9-12 M LiBr solution, and the salt is consequently removed using, for example, dialysis.

In some embodiments, a silk solution may then be concentrated using, for example, dialysis against a hygroscopic polymer, for example, PEG, a polyethylene oxide, amylose or sericin. In some embodiments, PEG is of a molecular weight of 8,000-10,000 g/mol and has a concentration of 25-50%. In some embodiments, any dialysis system can be used. In some embodiments, dialysis may be for a time period sufficient to result in a final concentration of aqueous silk solution between 10-30%, for example, dialysis for 2-12 hours.

In some embodiments, biocompatible polymers can also be added to the silk solution to generate composite matrices in the methods and processes of the present invention. Exemplary biocompatible polymers useful in the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). In some embodiments, two or more biocompatible polymers can be used.

In accordance with various embodiments, a silk solution may comprise any of a variety of concentrations of silk fibroin. In some embodiments, a silk solution may comprise 0.1 to 30% by weight silk fibroin. In some embodiments, a silk solution may comprise between about 0.5% and 30% (e.g., 0.5% to 25%, 0.5% to 20%, 0.5% to 15%, 0.5% to 10%, 0.5% to 5%, 0.5% to 1.0%) by weight silk fibroin, inclusive. In some embodiments, a silk solution may comprise at least 0.1% (e.g., at least 0.5%, 1%, 2%, 3%, 4%, 5%, 6%, 7%, 8%, 9%, 10%, 15%, 20%, 25%) by weight silk fibroin. In some embodiments, a silk solution may comprise at most 30% (e.g., at most 25%, 20%, 15%, 14%, 13%, 12%, 11%, 10%, 5%, 4%, 3%, 2%, 1%) by weight silk fibroin.

According to various embodiments, such as where provided compositions and methods are used to produce platelets, any of a variety of different bioactive materials or components (e.g., one or more functionalizing agents) may be entrapped or immobilized in a silk membrane to facilitate function and utility of the silk membrane. In some embodiments, provided silk membranes may be applied as a series of individual layers.

According to various embodiments, a porous silk membrane may be formed into any of a variety of shapes. In some embodiments, a porous silk membrane is a sheet (for example, a film), a tube, a sphere or portion thereof, or other application-appropriate shape.

As described herein, many embodiments will comprise a silk membrane configured such that the silk membrane forms a silk wall and defines a lumen. In some embodiments, a silk wall will have two sides, a lumen-facing side and an environment facing side (e.g., a matrix-facing side). By way of non-limiting example, in some embodiments, a silk membrane may be configured as a tube wherein the membrane defines a tubular silk wall and the interior of the tube comprises a lumen. As another example, in some embodiments, a silk membrane may be configured as a sphere, wherein the interior of the sphere comprises a lumen.

Various embodiments may comprise three dimensional silk membranes comprising pores of various sizes (i.e., porous silk membranes). In some embodiments, pores in a three dimensional silk membrane have a diameter between about 1-50 μm, inclusive. In some embodiments, pores in a three dimensional silk membrane have a diameter between about 5-25 μm, inclusive. In some embodiments, pores in a three dimensional silk membrane have a diameter between about 1-10 μm, inclusive.

In some embodiments, silk membranes are made porous through the use of one or more porogens. It is contemplated that any known porogen may be suitable for use according to various embodiments. In some embodiments, a porogen may be or comprise crystals (e.g., sodium chloride crystals), micro- and/or nano-spheres, polymers (such as polyethylene oxide, or PEO), ice crystals, and/or a laser. In some embodiments a porogen may comprise mechanical introduction of pores (e.g., using a needle or other article or device to pierce a membrane one or more times, or using stress to introduce one or more tears in the membrane).

In accordance with various embodiments, provided silk membranes (e.g., porous silk membranes) may be of a variety of different thicknesses. In some embodiments, a silk membrane is less than or equal to 100 μm thick. In some embodiments, a silk membrane is between 1 and 100 μm thick (e.g., 5-100, 10-100, 10-90, 10-80, 10-70, 20-70, 30-70, 40-70 μm thick). In some embodiments, a silk membrane is about 50-70 μm thick, inclusive. In some embodiments, a silk membrane is of a substantially uniform thickness. In some embodiments, a silk membrane varies in thickness across a silk wall.

Preparing Silk Membranes

According to various embodiments, provided silk membranes may be formed via any application-appropriate method. In some embodiments, for example, silk membranes are formed, at least in part, via deposition of a silk solution on a substrate, followed by a drying (e.g., air-drying) or other process. By way of non-limiting example, and a shown in the Examples below, in some embodiments, provided silk membranes are formed into tubes using steel rods as a substrate in order to provide a tubular shape to the silk membrane. In some embodiments, silk membranes are made via electrospinning (e.g., coaxial electrospinning, emulsion electrospinning, and/or melt electrospinning).

In some embodiments, the thickness of a silk membrane may be controlled by adjusting the concentration of fibroin in the silk fibroin solution used. For example, the more concentrated the fibroin in the aqueous silk fibroin solution is, the more fibroin that is deposited on the substrate and a more compact structure is formed.

Adjusting the pH of the aqueous silk fibroin solution may also affect the amount of fibroin deposited on the substrate. When the substrate is a negatively charged substrate, lowering the pH of the silk fibroin solution favors deposition of the silk fibroin onto the substrate. When the substrate is a positively charged substrate, increasing the pH of the silk fibroin solution favors deposition of the silk fibroin onto the substrate. At a low pH (e.g., 2.0) the silk fibroin chains have a net positive charge, which favors deposition on a negative substrate. In contrast, at a high pH (e.g., 12.5) the silk fibroin chains have a net negative charge, and thus, deposition on a negatively charged substrate is not favored.

According to various embodiments, a silk fibroin solution may be coated onto any substrate. In some embodiments, the substrate may be or comprise a natural or synthetic material. By way of non-limiting example, a substrate may be or comprise plastic, wood, glass, leather, cloth, synthetic fibers or any metal or alloy. In addition, according to various embodiments, the substrate may be of any size or shape.

In some embodiments, the concentration of salt is increased to favor deposition of silk fibroin onto a substrate (e.g., a rod) or onto previous layers of silk. Salt concentration can be increased by addition of any salt to a silk fibroin solution including, but not limited to, monovalent and divalent salts such as NaCl, KCl and $CaCl_2$. In some embodiments, salts are monovalent, such as NaCl and KCl. In some embodiments, the salt concentration is adjusted using NaCl.

In some embodiments, provided compositions and biomaterials may be sterilized using conventional sterilization process such as radiation based sterilization (i.e., gamma-ray) and/or chemical based sterilization. In some embodiments, the sterilization process will be with ethylene oxide at a temperature between 52-55° C. for a time of 8 hours or less. After sterilization the biomaterials may be packaged in an appropriate sterilized moisture resistant package for shipment.

Functionalizing Agents

According to various embodiments, a variety of functionalizing agents may be used. In some embodiments, a functionalizing agent may be any compound or molecule that facilitates the attachment to and/or development (e.g., growth) of one or more endothelial cells on a silk membrane. In some embodiments, a functionalizing agent may be any compound or molecule that facilitates the attachment and/or development (e.g., growth) of one or more megakaryocytes and/or hematopoietic progenitor cells on a silk matrix and/or silk membrane. In some embodiments, a functionalizing agent may be or comprise an agent suitable for facilitating the production of one or more of white blood cells and red blood cells.

In some embodiments, a functionalizing agent may be or comprise a cell attachment mediator and/or an extracellular matrix protein, for example: collagen (e.g., collagen type I, collagen type III, collagen type IV or collagen type VI), elastin, fibronectin, vitronectin, laminin, fibrinogen, von Willebrand factor, proteoglycans, decorin, perlecan, nidogen, hyaluronan, and/or peptides containing known integrin binding domains e.g. "RGD" integrin binding sequence, or variations thereof, that are known to affect cellular attachment.

In some embodiments, a functionalizing agent may be any soluble molecule produced by endothelial cells. Non-limiting examples include fibroblast growth factor-1 (FGF1) and vascular endothelial growth factors (VEGF).

According to some embodiments, a plurality of functionalizing agents may be used. For example, in some embodiments wherein production of platelets is desired, provided compositions may comprise the use of laminin, fibronectin and/or fibrinogen, and type IV collagen in order to facilitate the attachment and growth of endothelial cells on a silk membrane (e.g., a porous silk membrane) and/or attachment of megakaryocytes to a silk matrix.

In some embodiments, a functionalizing agent may be embedded or otherwise associated with a silk membrane and/or silk matrix such that at least a portion of the functionalizing agent is surrounded by a silk membrane and/or silk matrix as contrasted to a functionalizing agent simply being positioned along the surface of a silk membrane and/or silk matrix. In some embodiments, a functionalizing agent is distributed along and/or incorporated in substantially the entire surface area of a silk membrane/silk wall. In some embodiments, a functionalizing agent is distributed and/or incorporated only at one or more discrete portions of a silk membrane/wall and/or silk matrix. In some embodiments, a functionalizing agent is distributed in and/or along at least one of the lumen-facing side of a silk wall and the matrix-facing side of a silk wall.

According to various embodiments, any application-appropriate amount of one or more functionalizing agents may be used. In some embodiments, the amount of an individual functionalizing agent may be between about 1 µg/ml and 1,000 µg/ml (e.g., between about 2 and 1,000, 5 and 1,000, 10 and 1,000, 10 and 500, 10 and 100 µg/ml). In some embodiments, the amount of an individual functionalizing agent may be at least 1 µg/ml (e.g., at least 5, 10, 15, 20 25, 50, 100, 200, 300 400, 500, 600, 700, 800, or 900 µg/ml). In some embodiments, the amount of an individual functionalizing agent is at most 1,000 µg/ml (e.g., 900, 800, 700, 600, 500, 400, 300 200, 100, 90, 80, 70, 60, 50, 40, 30, 20, 10, or 5 µg/ml).

Stromal derived factor-1α

Various embodiments comprise stromal cell-derived factor I (e.g., SDF-1α), for example, where SDF-1α is associated with a silk membrane/wall and/or silk matrix.

SDF-1α is a CXC motif chemokine (i.e., a chemokine have two N-terminal cysteine residues separated by one amino acid) that is generally known to activate leukocytes and be induced by proinflammatory stimuli. During development, SDF-1α is thought to be involved in directing the migration of hematopoietic stem cells from the liver to the bone marrow, and also to be involved in the formation of blood vessels.

As described herein, in some embodiments, SDF-1α is used to stimulate the migration and/or development of megakaryocytes and/or endothelial cells along silk matrices and membranes. In some embodiments, SDF-1α may be embedded or otherwise associated with a silk membrane and/or silk matrix such that at least a portion of the SDF-1α is surrounded by a silk membrane and/or silk matrix, as contrasted to SDF-1α simply being positioned along the surface of a silk membrane and/or silk matrix. In some embodiments, SDF-1α is distributed along and/or incorporated in substantially the entire surface area of a silk membrane/silk wall. In some embodiments, SDF-1α is distributed and/or incorporated only at one or more discrete portions of a silk membrane/wall and/or silk matrix. In some embodiments, SDF-1α is distributed in and/or along at least one of the lumen-facing side of a silk wall and the matrix-facing side of a silk wall.

Any of a variety of amounts of SDF-1α may be used according to various embodiments. In some embodiments, the amount of SDF-1α may be between 100 ng/ml and 300 ng/ml (e.g., between 100 and 250, 100 and 200, 100 and 150, and/or 200 and 300 ng/ml).

In some embodiments of provided methods, association between SDF-1α and a silk membrane comprises immobilizing at least a portion of the stromal derived factor-1α and/or at least one functionalizing agent within a silk membrane (e.g., a porous silk membrane). In some embodiments, association between SDF-1α and a silk membrane comprises adsorbing at least a portion of the stromal derived factor-1α and/or at least one functionalizing agent onto a surface of the porous silk membrane.

Silk Matrices

Any of a variety of silk matrices are contemplated as useful in accordance with various embodiments. In some embodiments, a silk matrix may be a three dimensional structure comprising silk fibroin and a plurality of pores. In some embodiments, a silk matrix will have a porosity of between 50% and 99.5% (e.g., 70% to 99%), inclusive.

In some embodiments, silk matrices are characterized as having interconnected pores, biocompatibility, and/or pore sizes large enough to allow for cell growth. In some embodiments, a silk matrix will have a configuration and/or pore size sufficient to allow for the extension of proplatelets from a megakaryocyte therethrough, for example, through the silk matrix and into the lumen of a silk membrane. (e.g., about 300 μm to about 500 μm).

Provided silk matrices may be made/formed via any application-appropriate process. In some embodiments, a silk matrix may be created from a silk solution, such as the silk fibroin solutions as described above and/or previously known in the art. In some embodiments, a silk matrix may be made via leaching (e.g., salt leaching). In some embodiments, a silk matrix may be made via a solvent casting/particulate leaching process. In some embodiments, a silk matrix may be made via a freeze-drying process. In some embodiments, a silk matrix maybe made via a gelation process. In some embodiments, a provided silk matrix is made using two or more methods.

In some embodiments, a silk matrix is designed to mimic the extracellular matrices (ECM) of the body, such as, for example, through the addition of SDF-1α and/or one or more functionalizing agents. In some such embodiments, the matrix serves as both a physical support and an adhesive substrate for isolated cells during in vitro culture and subsequent growth. In some embodiments, as the transplanted cell populations grow and the cells function normally, they may begin to secrete their own ECM support.

In some embodiments, a silk matrix will comprise and/or be associated with a plurality of megakaryocytes. In some embodiments, megakaryocytes may migrate from one position on a silk matrix to another, for example, toward a silk wall of a silk membrane that is at least partially enveloped by the silk matrix.

Various embodiments comprise a silk matrix with pores of any of a variety of sizes. In some embodiments, the pores of a silk matrix have a diameter between about 5 μm and 1,000 μm, inclusive. In some embodiments, the pores of a silk matrix may have a diameter of between about 10 μm and 1,000 μm (e.g., 10 to 900, 10 to 800, 10 to 700, 10 to 600, 10 to 500, 100 to 500, 200 to 500, 300 to 500, 400 to 500). In some embodiments the pores of a silk matrix have a diameter of between about 300 and 500 μm, inclusive. In some embodiments, the pores of a silk matrix have diameters that are substantially similar in size across the matrix. In some embodiments, the pores of a silk matrix have diameters that vary significantly across the matrix.

According to various embodiments, a silk matrix is formed around at least a portion of a silk membrane. By way of non-limiting example, in some embodiments, a silk matrix is formed at least partially around a silk membrane which is in a tubular configuration so that at least a portion of the silk membrane is enveloped by the silk matrix. In some embodiments, substantially the entire silk membrane is enveloped by a silk matrix.

Platelet Producing Cell Sources

As described herein, including in the Examples below, some provided embodiments may be used to produce large numbers of differentiated and/or functional platelets. In some embodiments, any platelet producing cell source (e.g., megakaryocytes) may be used as a component of provided methods and compositions/systems. In some such embodiments, provided methods and compositions may comprise endothelial cells and/or megakaryocytes. In some embodiments, a platelet producing source may be or comprise a cell that is capable of becoming or giving rise to one or more megakaryocytes, for example, an embryonic stem (ES) cell or an induced pluripotent stem cell (iPS). In some embodiments, a platelet producing cell source may be derived from a natural source, for example, bone marrow or umbilical cord blood. In some embodiments, a platelet producing cell source may be isolated using any available method including, for example, apheresis.

While a variety of embodiments may be suitable for producing platelets, in some embodiments, provided compositions comprise a plurality of endothelial cells located at least partially within the lumen of a silk membrane. In some embodiments, the endothelial cells form a confluent monolayer, for example, the monolayer may be within the lumen of a silk membrane. In some embodiments, the confluent layer of endothelial cells exhibit a cobblestone morphology. In some embodiments, the confluent layer of endothelial cells exhibit VE-cadherin staining that localizes to the cell-cell junctions. In some embodiments, more platelets are produced per seeded cell (e.g., megakaryocyte) when in the presence of the endothelial cells as compared to a seeded cell not in the presence of endothelial cells. In some embodiments, about 30 to 3000 more platelets are produced per seeded cell (e.g., megakaryocyte) when in the presence of the endothelial cells as compared to a seeded cell not in the presence of endothelial cells. In some embodiments, about 50-fold to about 500-fold (e.g., about 50-fold, 75-fold, 100-fold, 200-fold, 300-fold, 400-fold or 500-fold) more platelets are produced from the system as compared to the same system without the confluent layer of endothelial cells in the same amount of time. In some embodiments, endothelial cells are selected from: human dermal microvascular endothelial cells, human umbilical vein endothelial cells, and primary human endothelial cells.

In some embodiments, provided compositions comprise a plurality of megakaryocytes located at least partially within the silk matrix. Generally, in vivo, megakaryocytes (Mks) associate with the bone marrow sinusoids where they convert their cytoplasm into long processes, called proplatelets, that protrude through the vascular endothelium into the lumen and release platelets. In vivo, shedding of proplatelet-like protrusions into blood vessel lumens has been visualized by multiphoton intravital microscopy in intact mouse bone marrow. The support of hematopoietic homeostasis typically relies on specialized cells and factors that constitute the hematopoietic 'niche' or microenvironment. Without wishing to be held to a particular theory, it is possible that this hematopoietic niche regulates a series of events leading to platelet release. However, the mechanisms by which these factors coordinate platelet production are incompletely known both in normal and disease conditions. In part due to this lack of knowledge, previous attempts to engineer an artificial tissue that reflects key features of the physiological bone marrow niche environment have not been satisfactory. In contrast, among the advantages provided by the present invention are: an improved understanding of the mechanistic and fundamental controls regulating Mk function, improved compositions and techniques for stimulating functional platelet formation, and the provision of compositions/systems for future modes for therapeutic inquiry (e.g., in vitro screening of therapeutic compounds).

In some embodiments, provided methods and compositions allow for the development of one or more confluent layers of viable and functional endothelial cells along a surface of a silk membrane and/or silk matrix.

Methods of Making Platelets

In some embodiments, the present invention provides methods of producing platelets including the steps of providing a silk membrane between about 30 μm and 100 μm thick, inclusive, contacting the silk membrane with a porogen to form a porous silk membrane comprising at least one silk wall defining a lumen, associating the porous silk membrane with stromal derived factor-1α and at least one functionalizing agent, forming a three dimensional silk matrix comprising interconnected pores wherein the pores have a diameter of between about 100 and 500 μm, inclusive, wherein the silk matrix is formed around at least a portion of the porous silk membrane, introducing a plurality of megakaryocytes to the silk matrix such that the megakaryocytes are located at least partially within the porous silk matrix, and stimulating the plurality of megakaryocytes to produce platelets.

In some embodiments, silk membranes, silk matrices, functionalizing agents, SDF-1α, porogens, and pore sizes used in provided methods may be as discussed elsewhere herein, including the Examples below. In some embodiments, provided methods include providing a plurality of endothelial cells, wherein the plurality of endothelial cells are located at least partially within the lumen of a silk membrane. In some embodiments, provided compositions are characterized at least in part by their ability to support the viability and/or function of a confluent layer of endothelial cells.

In some embodiments, a silk membrane may be functionally connected to a source of fluid (e.g., an infusion pump). In some embodiments a fluid is a circulating or other fluid that is in motion (e.g., a perfusate). In some embodiments, a fluid contains one or more growth factors, nutrients, functionalizing agents, and/or other material that is useful in supporting cell growth and/or viability. In some embodiments, a fluid is or comprises one or more of a cell culture medium, blood, and reconstituted red blood cells. In some embodiments, the fluid may comprise serum.

In some embodiments, provided methods and compositions may comprise a fluid, such as a perfusate, being circulated at a particular flow rate and/or shear rate. In some embodiments, a flow rate may be between about 20 μL/min and 250 μL/min (e.g., 25 μL/min to 200 μL/min, 25 μL/min to 150 μL/min, 25 μL/min to 100 μL/min, 50 μL/min to 200 μL/min, 50 μL/min to 150 μL/min, 50 μL/min to 100 μL/min, 75 μL/min to 200 μL/min, 75 μL/min to 150 μL/min, 75 μL/min to 100 μL/min). In some embodiments, the fluid may be flowing through the system at a flow rate of about 20 μL/min to 250 μL/min. In some embodiments, the fluid may flow through the system at a flow rate of about 32 μL/min for about 24 hours before the platelets are collected. In another embodiment, the fluid may flow through the system at a flow rate of about 94 μL/min for at least about 6 hours before the platelets are collected In some embodiments, a shear rate may be between about 30/s and 300/s (e.g., 30 to 250, 30 to 200, 30 to 150, 30 to 100/s). In some embodiments, a shear rate is at least about 30/s. In some embodiments, a shear rate is at most about 300/s. In some embodiments, a shear rate is about 60/s. In some embodiments, provided methods and compositions are at least partially characterized in that they are able to produce a high proportion of differentiated and/or functional platelets. In some embodiments, megakaryocytes used in provided methods and compositions produce platelets wherein at least about 70% (e.g., at least about 75%, 80%, 85%, 90%, 95%) of the platelets produced express CD61. In some embodiments, megakaryocytes used in provided methods and compositions produce platelets wherein at least about 50% (e.g., 60%, 70%, 80%, 90%) of the platelets produced express at least one of CD61, CD42, and CD41. In some embodiments platelets produced exhibit a similar morphology as compared to platelets isolated from peripheral blood. In other embodiments, platelets produced bind PAC-1. In some embodiments, platelets produced bind PAC-1 following stimulation with thrombin, ADP and/or epinephrine.

In some embodiments, provided methods and compositions are at least partially characterized in that they are able to produce a surprisingly high yield of platelets. This high yield of platelets has not previously been achieved in the art. For instance Pallotta et al. report that the yield of collected platelets from their system which utilized silk tubes was only 200+/−50 per megakaryocyte that extended proplatelets in 16 hours (Tissue Engineering (2011) 17:1223-1232). In some embodiments, the high yield of platelets produced by the compositions and methods of the present invention are about $0.5 \times 10^6$ to $4.0 \times 10^6$ platelets (e.g., about $0.5 \times 10^6$ to $3.5 \times 10^6$, about $0.5 \times 10^6$ to $3.0 \times 10^6$, about $0.5 \times 10^6$ to $2.0 \times 10^6$, about $0.5 \times 10^6$ to about $1.5 \times 10^6$, about $0.8 \times 10^6$ to $3.5 \times 10^6$, about $0.8 \times 10^6$ to $3.0 \times 10^6$, about $0.8 \times 10^6$ to $2.5 \times 10^6$, or about $0.8 \times 10^6$ to $2.0 \times 10^6$). In some embodiments, the platelets are produced in about 1 hour, about 2 hours, about 3 hours, about 4 hours, about 5 hours, about 6 hours, about 7 hours, about 8 hours or longer. In some embodiments, the methods and compositions are characterized in that about $0.8 \times 10^6$ to $2.0 \times 10^6$ are produced in about 6 hours. In some embodiments, the methods and compositions are characterized in about $0.13 \times 10^6$ to $0.33 \times 10^6$ platelets are produced per hour.

In some embodiments, the viability and/or functionality of platelets produced by provided methods and compositions may be characterized by one or more of the following: analysis of platelet adhesion on a substrate, analysis of platelet activation in response to one or more platelet agonists, analysis of platelet aggregation, analysis of platelet spreading under shear stress, and analysis of thrombus formation under shear stress. In some embodiments, platelets produced by provided methods and compositions may be characterized via one or more in vivo assessments. In some embodiments, an in vivo assessment may be or comprise platelet reconstitution after irradiation (e.g., in mice).

Additional exemplary methods of characterizing platelet viability and/or functionality of platelets produced by provided methods and compositions may be found, inter alia, in Harrison P, Platelet function analysis, 2005, *Blood Rev.*, 19:111-123, the disclosure of which is hereby incorporated in its entirety.

EXAMPLES

Example 1

A Microphysiologic System for Platelet Production

Materials and Methods

This Example provides, among other things, evidence that provided systems and methods represent a new microphysiological platform for the production of, in this Example, platelets. Provided systems in this Example were able to facilitate and support megakaryocyte migration and production of platelets into an artificial blood vessel lumen (created from a porous silk membrane). Unless otherwise specified, the methods used in this Example are as follows:

Silk Solution

Silk fibroin was extracted from *Bombyx mori* silkworm cocoons according to previously published literature. Briefly, *B. mori* cocoons were de-wormed and chopped. The chopped cocoons were boiled for 30 minutes in 0.02 M $Na_2CO_3$ solution at a weight to volume ratio of 5 g to 2 L. The fibers were rinsed for 20 minutes for three times in distilled water and dried overnight. The dried fibers were solubilized for four hours at 60° C. in 9.3 M LiBr at a weight to volume ration of 3.5 g to 14 mL. The solubilized silk solution was dialyzed against distilled water using a Slide-A-Lyzer cassette (ThermoScientific) with a 3,500 MW cut-off for three days and changing the water a total of eight times. The silk solution was centrifuged at 3220 g for 10 minutes and repeated twice to remove large particulates and stored at 4° C. The concentration of the silk solution was determined by drying a known volume of the solution and massing the remaining solids.

Silk Membrane/Film Fabrication

Silk solution (1% w/v) containing polyethylene oxide (PEO) porogen (0.035% w/v; 900,000 MW, Sigma) was cast on polydimethylsiloxane (PDMS; Dow Corning) molds (45 µL $cm^{-2}$ of mold surface area) and dried at 37° C. for 16 hours. Extracellular matrix (ECM) proteins were added to the silk film, either immobilized within the silk film or adsorbed to the film surface Immobilized ECM silk films were prepared by mixing the ECM component with the silk prior to casting. Adsorbed ECM silk films were incubated with the ECM component overnight at 4° C. The following ECM components were used: 50 µg $mL^{-1}$ fibronectin (human plasma, BD Biosciences), 50 µg $mL^{-1}$ collagen type I (human, Sigma), 50 µg $mL^{-1}$, laminin (human, Sigma), 500 µg $mL^{-1}$ fibrinogen (human, CalBioChem). Silk films were water annealed in a vacuum chamber containing 100 mL of water at the bottom of chamber. The water annealing chamber was maintained at either 22° C. for 8 hours or 4° C. for 2 hours to achieve 'medium' and 'low' silk film mechanical properties, respectively. Silk films were lifted off the PDMS mold and exposed to ultraviolet light for 30 minutes per side inside of a sterile biological hood.

For co-culture experiments, the membrane from Transwell inserts (Sigma) was removed under sterile conditions using a 5 mm biopsy punch. Silk films were trimmed using an 8 mm diameter biopsy punch and secured to the Transwell insert using a sterile, medical-grade silicon grease (Dow Corning). The films were rinsed three times in PBS overnight at 4° C. For experiments not performed in Transwell inserts, films were secured between two rings of scotch tape (6 mm inner diameter, 12 mm outer diameter) according to previously described methods, which assisted in handling of the sample. To prevent the films from floating during cell culture, films were secured to the bottom of 24-well plates using silicon rings (10 mm inner diameter, 15.5 mm outer diameter, McMaster Carr). All samples were sterilely washed three times in PBS over the course of 24 hours to remove the PEO porogen. To induce 'high' β-sheet content, samples were soaked for three hours in 100% methanol and rinsed five times in PBS. Prior to cell seeding, silk films were soaked in cell culture media for one hour. A schematic summary of the system assembly is reported in FIG. 1.

Cell Isolation from Cord Blood

Megakaryocytes were differentiated from human umbilical cord blood-derived CD34+ cells using previously described methods (Balduini, 2008). Cord blood samples were purchased from the New York Blood Bank. Briefly, 35 mL of human cord blood was layered on 15 mL of lympholyte (Ficoll) and centrifuged at 515 g for 30 minutes at room temperature. The mononuclear cells were collected and washed twice with PBS. CD34+ cells were separated by an immunomagnetic technique (Miltenyi, Germany). The CD34+ cells were plated and cultured for 12 days in Stem Span media supplemented with 10 ng/mL thrombopoietin (TPO), interleukin (IL)-6, and IL-11, and 1% penicillin-streptomycin. Media was changed every three days.

Endothelial progenitor cells (EPCs) were differentiated from human umbilical cord blood-derived CD34+ cells using a method described previously (Ingram, 2004). Briefly, CD34+ cells were plated in EGM2-MV media (Lonza, Basel, Switzerland) in collagen type I-coated dishes (BD Biosciences) at an approximate density of $10 \times 10^3$ cells $mm^{-2}$. Non-adherent cells were removed after 36-48 hours. The media was changed every 2-3 days for four weeks until colonies reached confluence. Cells were trypsinized and expanded in flasks coated with collagen type I (rat tail, BD Biosciences).

Cell Culture

For both single and co-culture studies, megakaryocytes (Mks) were seeded at an approximate density of $250 \times 10^3$ cells $cm^{-2}$ in Stem Span (StemCell Technology, Vancouver, Canada) media supplemented with 10 ng/mL TPO, and 1% penicillin-streptomycin. Endothelial cells were seeded at an approximate density of $715 \times 10^3$ cells $cm^{-2}$ in EGM2-MV media. For indirect co-culture, EPCs were seeded onto coverslips on the bottom of a 24-well culture plate. For direct co-culture, EPCs were seeded on the bottom of the basement membrane model in 50 µl of media. EPCs were allowed to attach for two hours before flipping the Transwell insert right side up into a 24-well culture plate. EPCs were cultured for 24-36 hours until confluence was reached before seeding Mks in the upper chamber of the Transwell insert after which the media used was Stem Span media supplemented with TPO and penicillin-streptomycin.

Immunoassays

For immunofluorescence, samples were fixed in 4% neutral buffered paraformaldehyde, permeabilized in 0.5% Triton-X, and blocked with 3% bovine serum albumin. For monoculture studies MKs were probed with mouse anti-α-tubulin (1:700,Sigma) and goat anti-CD61 (1:50, Santa Cruz Biotechnology) antibodies. For co-culture studies MKs were probed with mouse anti-CD61 and EPCs were probed with rabbit anti-VE-Cadherin (1:200, Thermo Scientific). Nuclei were stained with Hoescht33258. Adhered Mks were determined by counting the number of cells co-expressing CD61 and α-tubulin in eight fields of view using a 40× objective on a fluorescent microscope (Olympus, Deutschland GmbH, Hamburg, Germany) Cells extending proplatelets were counted and the percentage of cells extending proplatelet was calculated (referred to as % PPF).

Silk Matrix/Sponge Preparation and Use

Figure 2:
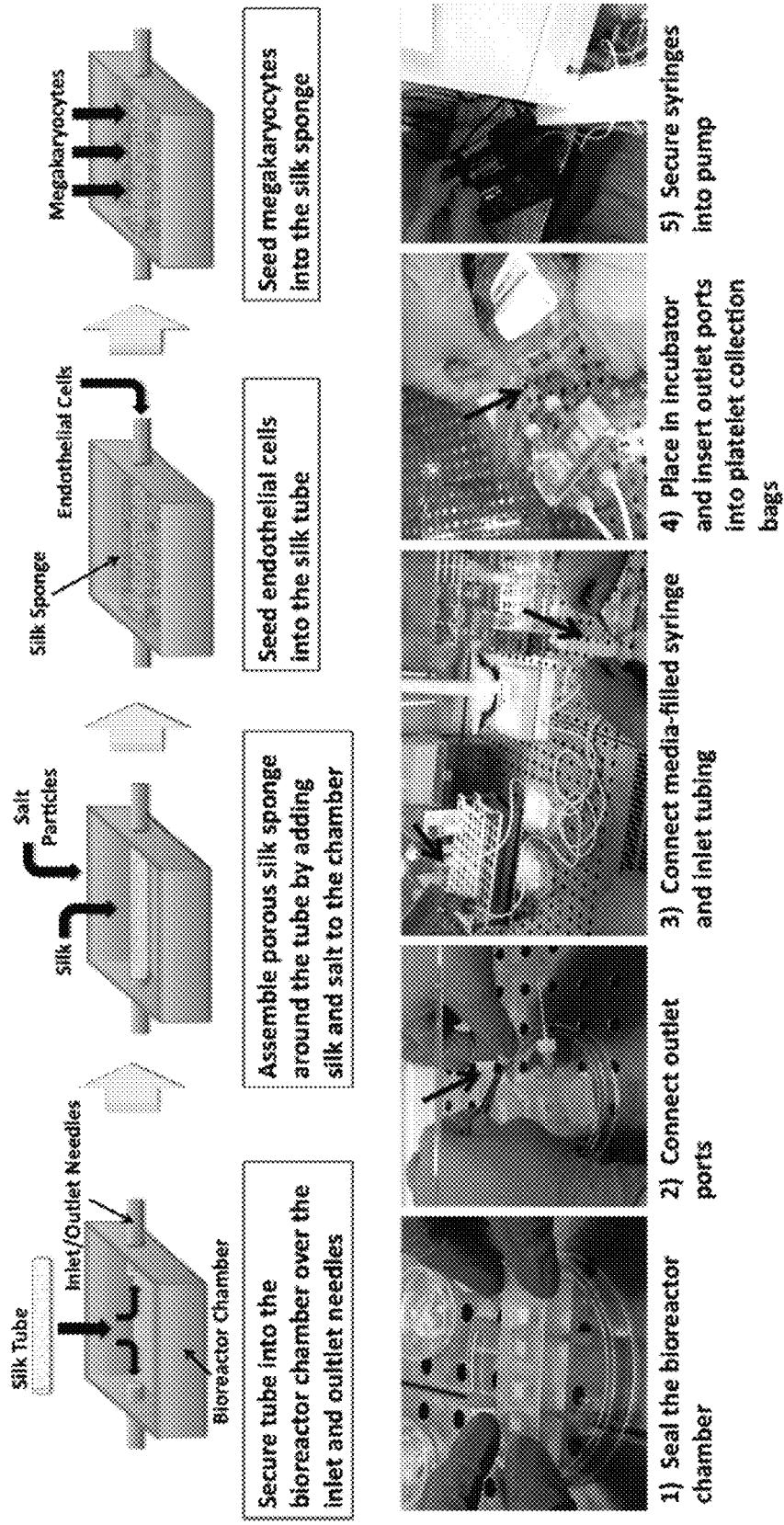
FIG. 2 shows a flow diagram and pictures of an exemplary method of constructing provided compositions and systems.

Porous silk tubes were prepared from a solution of 15% wt/v silk. PEO porogen was added to the silk solution for a 5% wt/wt of PEO to silk. Silk tubes were functionalized with 50 μg mL$^{-1}$ fibronectin (human plasma, BD Biosciences), 50 μg mL$^{-1}$ collagen type IV (human, Sigma), 50 μg mL$^{-1}$, laminin (human, Sigma), and/or 300 ng mL$^{-1}$ stromal cell-derived factor-1 (SDF-1). Tubes were fabricated by coating stainless steel wires (23 G) with the silk solution; the wires were first dipped in the silk solution and then submerged into a 100% methanol solution for 10 seconds. The coating was air dried for approximately 5-10 minutes after which point the dipping and air drying processes were repeated. Silk tubes were fabricated from a total of 1-3 dips. The coated wires were then submerged in PBS for approximately 30 minutes. The silk tubes were then gently removed from the wires by sliding them off, and then stored for up to 2-3 weeks at 4° C. Tubes were then trimmed to approximately 1.5 cm in length and secured into a perfusion bioreactor. The tubes were connected to blunt end needles at both ends (FIG. 2).

Figure 3:
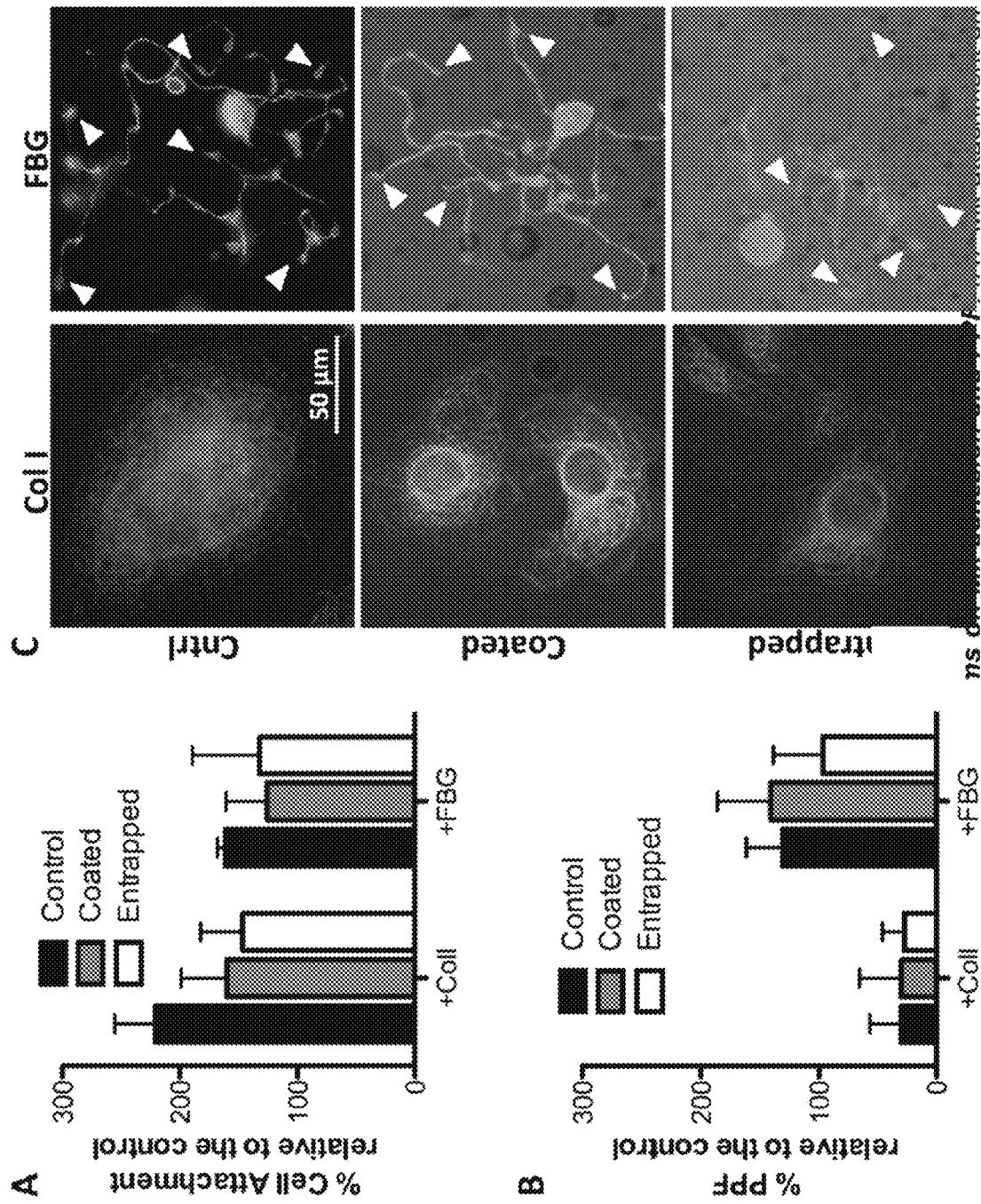
FIG. 3A-C show the effect of certain functionalized embodiments on megakaryocyte adhesion and proplatelet formation. Panel A shows megakaryocyte (Mk) attachment on functionalized silk membranes/films. Panel B shows proplatelet formation on functionalized silk membranes/ films. Panel C shows exemplary fluorescent images of Mk cultured on functionalized silk membranes/films.

A porous silk sponge was then assembled around the tube using a salt-leeching process. A 6% silk solution was dispensed around the tube and then NaCl particles (500-600 μm) were sifted into the silk solution in a ratio of 1 mL of 6% silk solution to 2 g of Na$_2$Cl particles. The tubes and scaffolds were placed at room temperature for 48 hours and then soaked in distilled water for 48 hours to leech the Na$_2$Cl particles. Scaffolds were trimmed to 5 mm in width and sterilized in 70% ethanol for 24 hours. Scaffolds were rinsed five times in PBS over 24 hours. Scaffolds were functionalized by incubating the scaffold in 50 μg mL$^{-1}$ fibronectin at 4° C. overnight. The tubes were seeded with endothelial cells over the course of 48 hours; approximately 200,000 endothelial cells were seeded into the tube and incubated overnight at 37° C., 5% CO$_2$. On the following day the bioreactor was flipped and another 200,000 endothelial cells were seeded into the tube and incubated overnight. MKs were seeded into the scaffold surrounding the tube (approximately 1.5-2.0×10$^6$ MKs per scaffold). In some experiments the MKs were seeded in the presence of Matrigel. The bioreactor inlet was connected to an infusion pump (Harvard Apparatus) and pumped at 32 μL min$^{-1}$ and the bioreactor outlet was connected to a platelet collection bag containing ACD (FIG. 3).

Platelet Analysis

Platelets were collected from the chamber below the Transwell insert and centrifuged at 1578 g for 15 minutes with 1 uM PGI2 (Cayman Chemical). The pellet was resuspended in Tyrode's buffer (supplemented with Mg and Ca) and incubated for 30 minutes at 37° C. Each sample was divided in two and one was activated with 3 U/ml of thrombin for three minutes at 37° C. The samples were probed with FITC PAC-1 for five minutes at 37° C. Samples were analyzed for forward and side scatter with using a flow cytometer (Navios, Beckman Coulter). The number of platelets was counted using a TruCount™ bead standard.

Results

Effects of Silk ECM Component Functionalization on Mk Development

Megakaryocytes (Mks) have been extensively studied for cell adhesion and PPF on collagen type I (Col I) and fibrinogen (FBG) substrates (Chen, 2007; Balduini, 2008; Malara, 2011). On Col I, Mk adhesion increases and PPF decreases compared to an uncoated substrate. On FBG, Mk adhesion increases and PPF increases compared to an uncoated substrate. In this study, silk membranes/films were functionalized by entrapment of Col IV and FBG within the film or by coating the silk membrane/film with Col IV and FBG. As reported in FIG. 3 silk membranes/films entrapped with different ECM components exerted different effect on Mk behavior, while both ECM components enhanced adhesion, Col IV inhibited PPF and, on the opposite, FBG promoted the process. Thus, by functionalizing silk, we can control Mk function on silk membranes/films.

Silk Matrix/Sponge-Based Bioreactor

Figure 4:
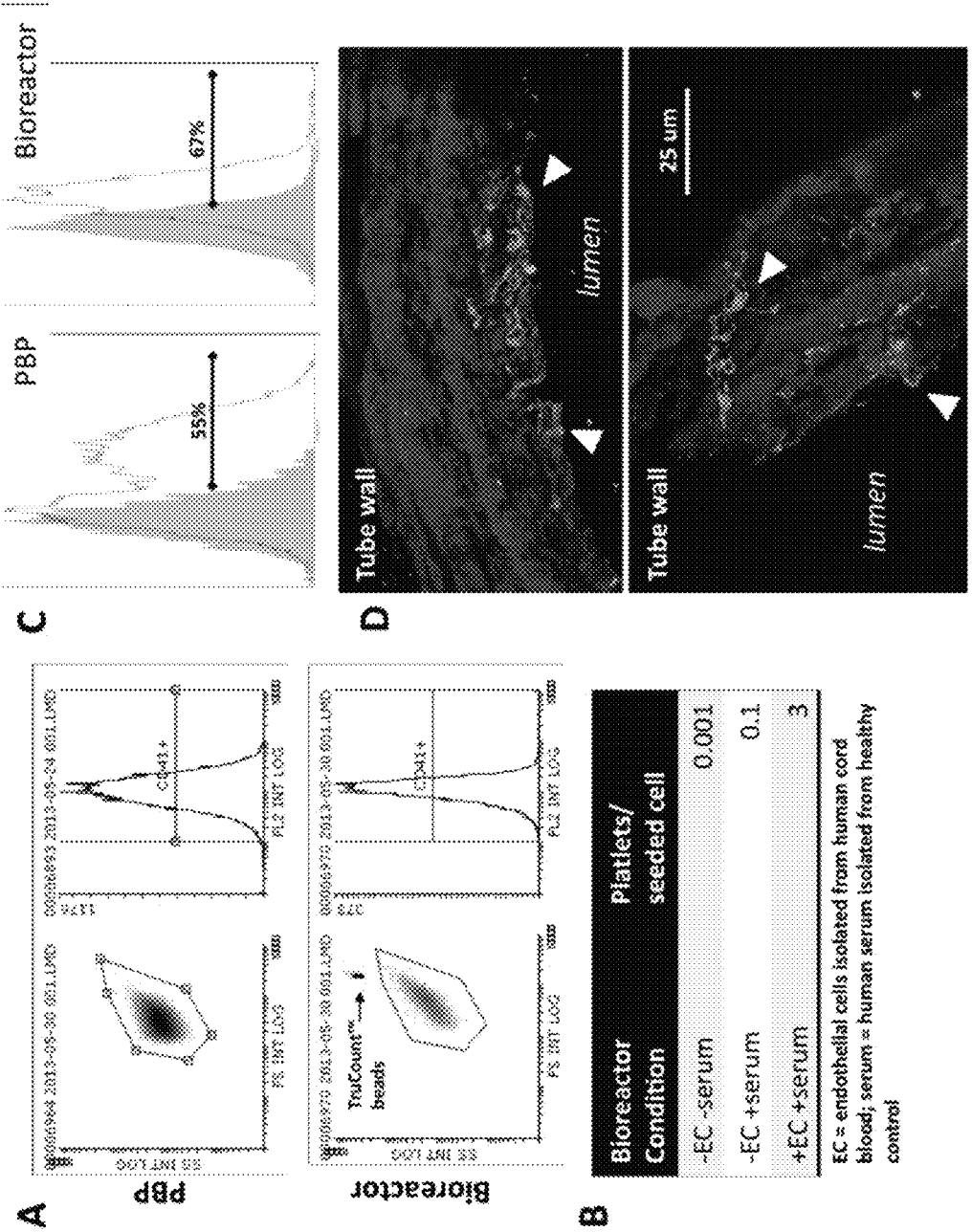
FIG. 4A-D show exemplary data regarding the characteristics of platelets, endothelial cells, and megakaryocytes produced in accordance with certain embodiments. Panel A shows that platelets produced in accordance with certain embodiments exhibit similar morphology and CD41 positive staining as peripheral blood platelets (PBP) control cells. Panel B shows that megakaryocytes seeded with human serum in provided porous silk membranes comprising endothelial cells generated higher numbers of platelets than those grown with no endothelial cells. Panel C depicts exemplary graphs showing that platelets collected from provided compositions and systems exhibited similar activation as compared to PBP controls. Panel D shows exemplary fluorescent microscopy images of megakaryocytes extending proplatelets through the silk wall of provided porous silk membranes.

In order to more closely mimic the bone marrow vascular niche structure, a porous silk sponge was assembled around the silk vessel-like tubes. Megakaryocytes seeded in the porous silk sponge at day 13 of differentiation migrated toward the silk tube and released platelets into the tube lumen. The perfusion bioreactor moved the platelets into the platelet collecting bags. After 24 hours of perfusion the platelets were collected and analyzed by flow cytometry. The bioreactor platelets exhibited similar morphology, CD41 positive staining, and activation compared to PBP controls (FIG. 4). Fluorescence microscopy images of megakaryocytes extending proplatelets through the silk tube wall.

Example 2

Scalable Silk Protein Platforms for Highly Efficient Functional Human Platelet Production This Example shows, among other things, that various embodiments provide the first known ex vivo high-throughput methods and compositions/systems for the production of functional platelets. Provided methods and compositions are able to provide platelets at an order of magnitude greater numbers per unit of time than previously existing methods and systems.

Figure 5:
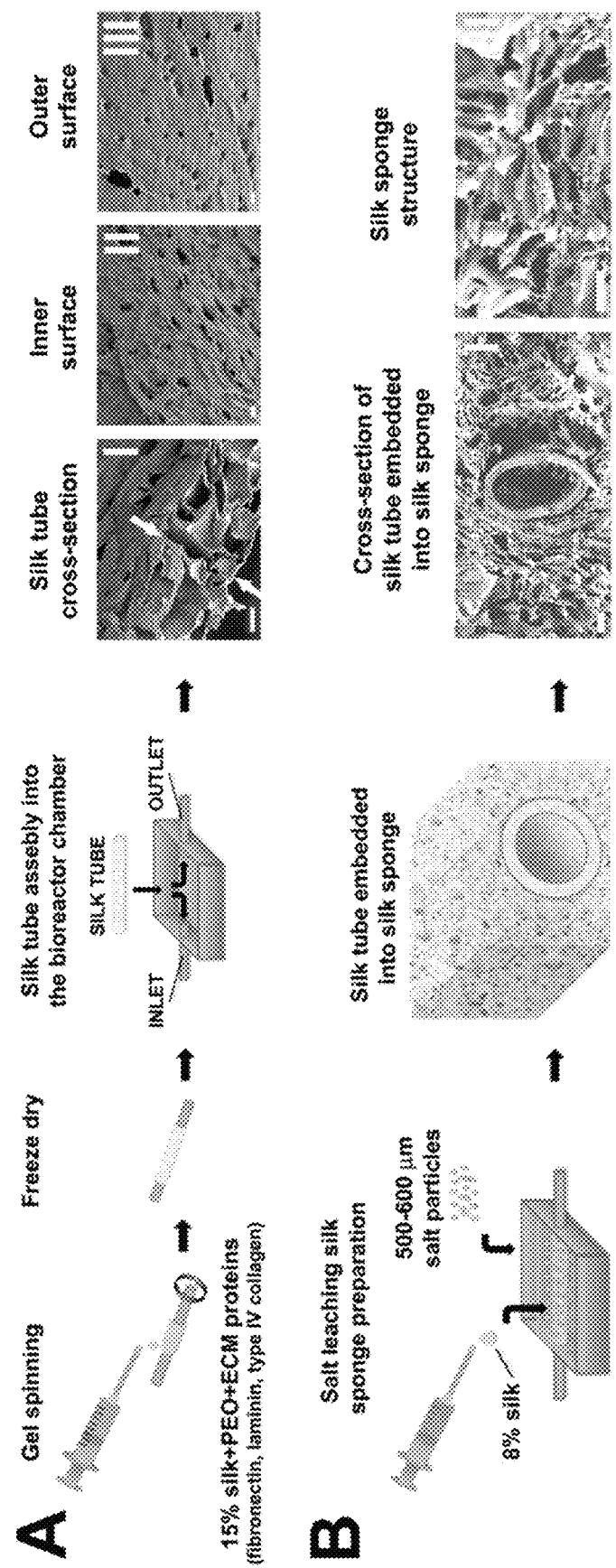
FIG. 5A-B shows flow diagrams of exemplary provided methods. Specifically, Panel A describes a method wherein silk porous membranes, here in the form of tubes, were prepared by gel spinning aqueous silk solutions containing a polyethylene oxide (PEO) porogen around a wire and functionalized via entrapment of physiologically relevant extracellular matrix (ECM) components (laminin, fibronectin, type IV collagen). The gel spun silk was freeze-dried, removed from the wire and soaked in water to leach out the PEO porogen. The resulting porous silk tubes were fitted into the bioreactor chamber over the inlet and outlet needles. (A I) SEM cross sections of a silk tube: the tube wall thickness was 97±26 µm with tube wall pore diameters of 22±4 µm to allow proplatelet elongation through the tube wall (scale bar=20 µm). Arrows indicate silk tubes borders (A II and III). SEM images showing pores on both the inner and outer surfaces of the silk tubes, respectively. Pores diameter was 6±2 µm (scale bars=20 µm). Panel B shows a method wherein aqueous silk was dispensed into the chamber around the tube and salt particle porogens were added. After leaching out the salt porogens, the resulting porous silk matrix/sponge was trimmed and sterilized. (B I) SEM images showing a silk tube embedded into the silk sponge (scale bar=100 µm). (B II) SEM images showing the porous structure of silk sponge (scale bar=100 µm).
Figure 9:
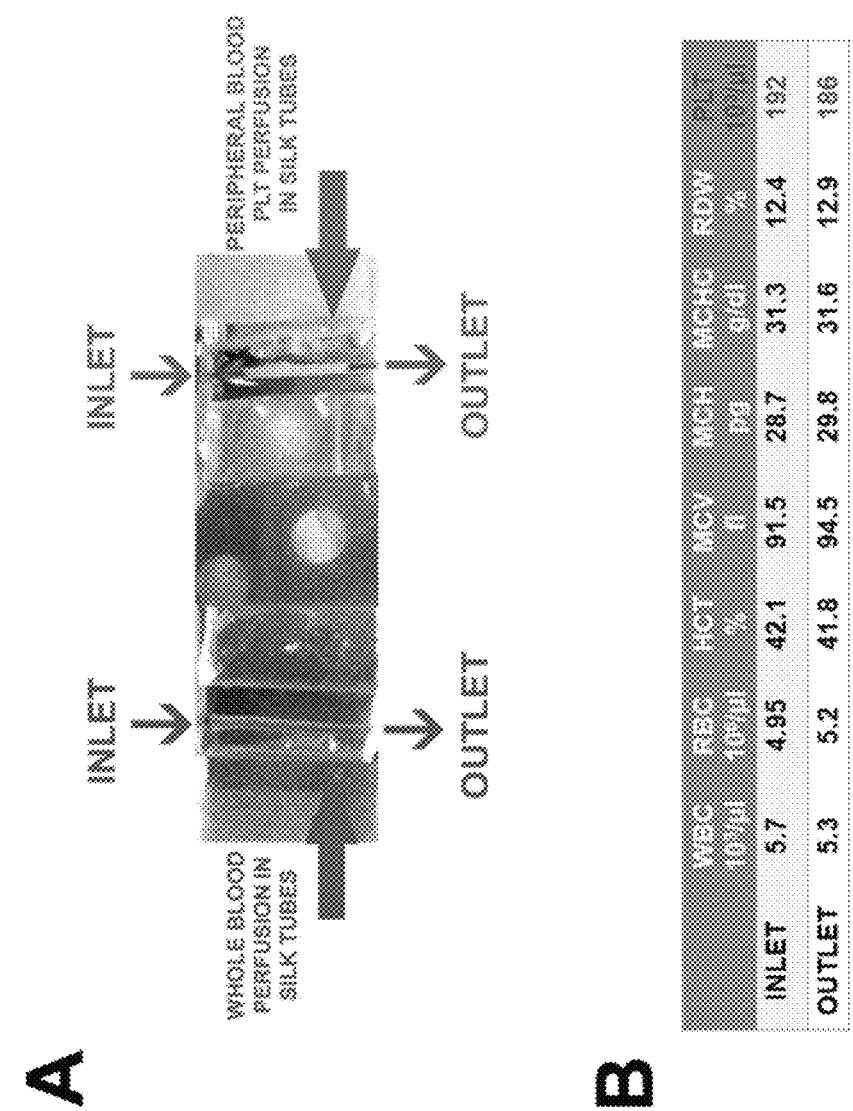
FIG. 9A-D shows an exemplary analyses of peripheral blood constituents and platelet functionality after perfusion of silk membranes/microtubes. Panel A shows whole blood (red) or peripheral blood platelets suspended in culture medium (pink) that were perfused into functionalized silk microtubes (tubular silk membranes). Panel B shows a representative analysis of whole blood constituent of one sample before (inlet) or after (outlet) perfusion. Panel C shows the result of an exemplary flow cytometry analysis of peripheral blood platelet basal activation before perfusion into a silk microtube. PAC-1 binding was used as a platelet activation marker. Panel D shows an exemplary flow cytometry analysis of peripheral blood platelet basal activation after perfusion into a silk microtube. Activation with thrombin or ADP demonstrated increased PAC-1 binding indicating that CD42+ platelet functionality was unchanged after passage through a silk microtube lumen. WBC=white blood cells; RBC=red blood cells; HCT—hematocrit; MCV=mean corpuscular volume; MCH=mean corpuscular hemoglobin; MCHC=mean corpuscular hemoglobin concentration; RDW=red blood cell distribution width; PLT=platelet.

In this Example, silk was used as a naturally-derived and tunable biomaterial to develop an in vitro tissue model of the bone marrow microvascular niche. Silk tubes were fabricated using a gel spinning method (see Lovett et al., 2008, Gel spinning of silk tubes for tissue engineering, *Biomaterials*, 29: 4650-4657) and exhibited physiologically relevant wall thickness (97±26 μm) with interconnected pores (22±4 μm in diameter), as analyzed by scanning electron microscopy (SEM) (FIG. 5A I-III). The silk tubes were functionalized via entrapment of physiologically relevant extracellular matrix (ECM) components (laminin, fibronectin, type IV collagen). Continuous platelet production by bone marrow Mks is consequent to cell migration toward sinusoidal vessels in response to stromal derived factor (SDF)-1α chemo-attraction, thus the silk tubes were also functionalized with 300 ng/mL SDF-1α. Finally, to mimic the bone marrow that surrounds the microvasculature, a porous silk sponge, consisting of interconnected pores approximately 100-500 μm in diameter, was assembled around the functionalized silk tubes (FIG. 5B). The biocompatible and non-thrombogenic properties of silk were demonstrated by perfusion of peripheral blood into the silk tubes at shear rate of 60/s. As shown in FIG. 9 cells from whole peripheral blood samples did not adhere to the silk vascular tube inner wall under flow (FIG. 9A, B) and isolated platelets remained quiescent and maintained their capability of responding to physiological stimuli from thrombin and adenosine diphosphate (ADP) after passage through the functionalized tubes, as demonstrated by PAC-1 binding (FIG. 9A, C, D). Additionally, no clotting was observed inside the silk vascular tubes.

Figure 6:
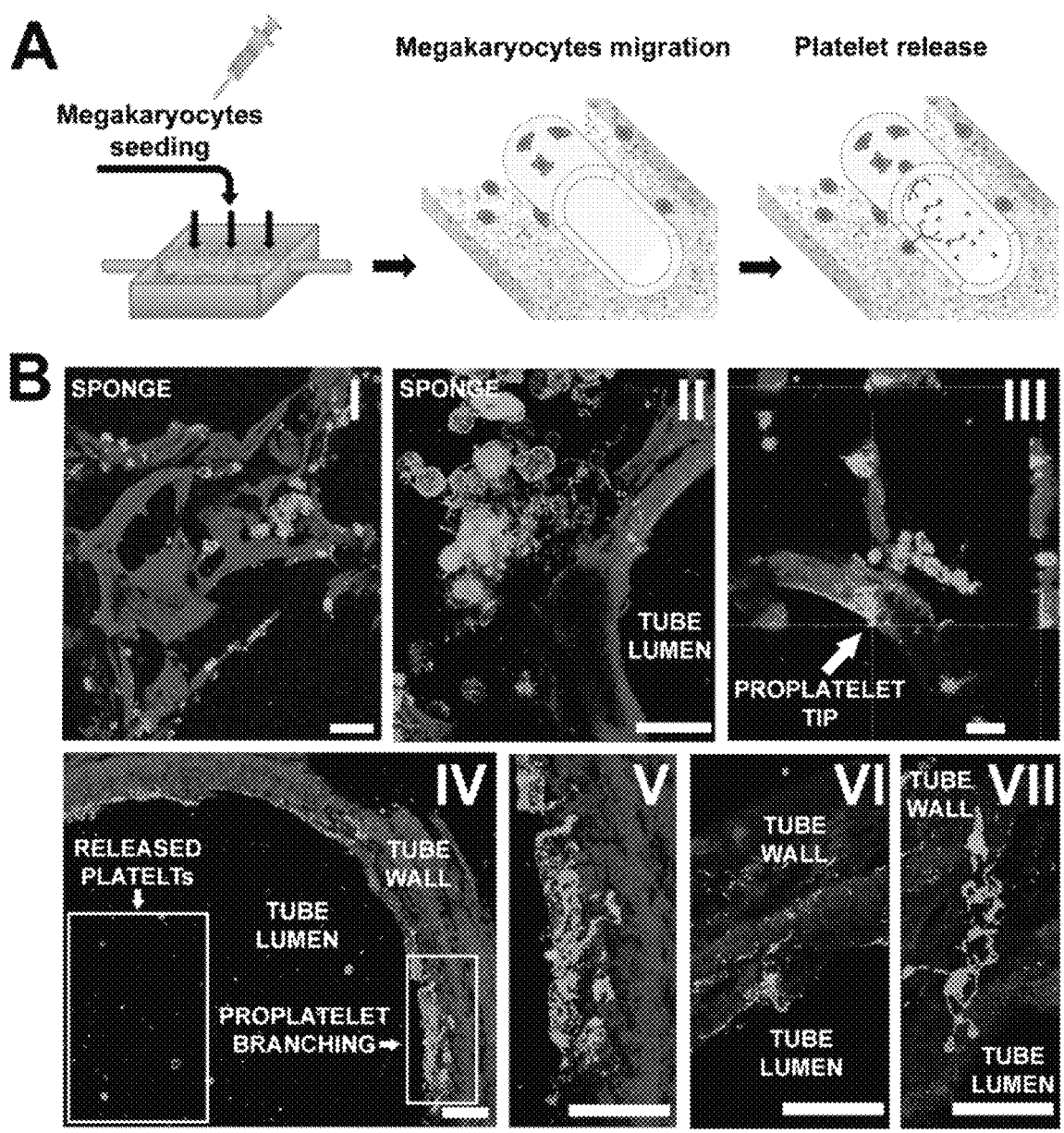
FIG. 6A-B proplatelet formation and platelet production from megakaryocytes as provided by certain embodiments. Specifically, panel A shows that after seeding into the silk matrix/sponge Mks migrated towards the tube, adhered and extended proplatelets through the membrane/tube wall to release platelets into the tube lumen. Panel B I shows representative confocal microscopy image of mature Mks immediately after seeding into the silk sponge. Mks localized into the silk sponge pore walls (green=CD61; blue=nuclei; scale bar=100 µm). Panel B II shows that, during the course of 24 hours, Mks migrated towards the tube. Confocal microscopy analysis shows mature Mks in close contact with the tube wall and elongating proplatelets through the tube wall (green=CD61; blue=nuclei; scale bar=50 µm). Panel B III shows that proplatelet-forming Mks extend proplatelets through the silk tube wall. Orthogonal projections showed proplatelet branches elongating through tube walls with proplatelet tips protruding into the tube lumen (green=CD61; blue=nuclei; scale bar=50 µm). Panel B IV, in the highlighted boxes shows proplatelet-forming Mk detectable along the inner wall of the silk tube and platelets released directly into the tube lumen (green=CD61; blue=nuclei; scale bar=50 µm). Panel B V shows magnification of the proplatelet-forming Mk shown in the "proplatelet branching" box of panel B IV (green=CD61; blue=nuclei; scale bar=50 µm). Panels B VI and VII show representative images of proplatelet branches into the porous silk tube wall (green=CD61; blue=nuclei; scale bar=50 µm). The structure of the silk sponge and tube were visualized in blue due to non-specific binding of Hoechst, the nuclear dye, to silk.
Figure 7:
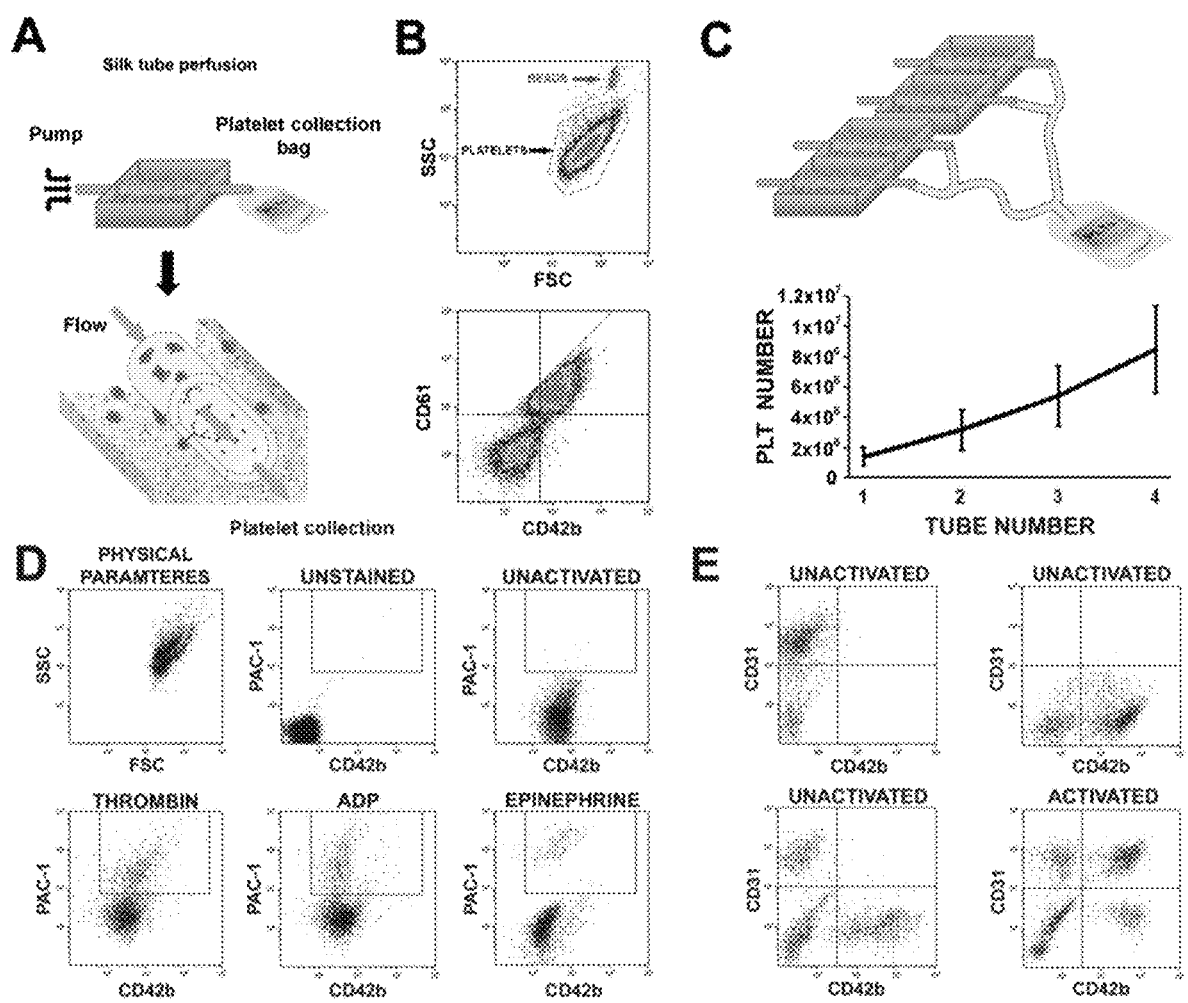
FIG. 7A-E shows the results of exemplary analyses performed on platelets provided according to some embodiments. Panel A shows silk tubes were perfused with culture media for additional 6 hours after Mk migration and the released platelets were collected into bags. Panel B shows in vitro produced platelets were analyzed with the same physical parameters as human peripheral blood platelets. Samples were mixed with counting beads in order to quantify the number of platelets which were identified as $CD61^+CD42b^+$ events. Panel C shows platelet release after perfusion of an increasing number of bioreactors with a maximum of four different silk tubes perfused concurrently. The graph shows the absolute number of platelets released per tube embedded in the silk sponge containing $2.5 \times 10^5$ Mks. Panel D shows collected platelets after bioreactor perfusion exhibited increased PAC-1 binding after thrombin, ADP and epinephrine stimulation. Panel E shows exemplary aggregation measurements by flow cytometry after stimulation with a cocktail of thrombin, ADP and epinephrine. Platelets were separately labeled with CD31 or CD42b (left and right top, respectively). The bottom panel shows dot plots of the mixed 1:1 platelets, respectively labeled with CD31 or CD42b, before (left) and after (right) platelet aggregation following stimulation with the agonist cocktail. The double-colored population indicates that the bioreactor platelets maintained the functionality to aggregate after perfusion through the silk tube.

A total of $2.5 \times 10^5$ mature Mks, derived from umbilical cord blood hematopoietic progenitors, were seeded in silk sponges for 24 hours at 37° C. in a 5% $CO_2$ atmosphere (FIG. 6A) Immediately after seeding, the Mks distributed heterogeneously in the porous silk sponge (FIG. 6B I), and after 24 hours Mks were preferentially located around the outer wall of the silk vascular tubes (FIG. 6B II). Further, Mks distributed along the external wall of the tubes elongated normally branched proplatelets across the tube walls with platelet tips protruding into the tube lumen (FIG. 6B III-VII). To mimic blood flow, the silk tubes were perfused for 6 hours with culture medium using a syringe pump at 94 µL/min, corresponding to a shear rate of 60/s. The flow through of the vascular tubes was collected into gas permeable-collection bags containing acid citrate dextrose (ACD) as anticoagulant (FIG. 7A). Collected platelets were double stained with anti-CD61 and anti-CD42b antibodies and exhibited similar physical parameters as normal human peripheral blood platelets as determined by flow cytometry analysis (FIG. 7B). The number of $CD61^+CD42b^+$ collected platelets was $1.4 \pm 0.6 \times 10^6$ per 3D tissue perfusion system and was linearly increased by the use of multiple bioreactors in parallel (FIG. 7C). Collected platelets were determined to be functional based on increased PAC-1 binding to the activated integrin $\alpha IIb\beta 3$ upon physiologic stimulation with both strong (i.e. thrombin) and weak (i.e. ADP, epinephrine) agonists (FIG. 7D). Platelet functionality was further confirmed by a flow cytometry-based platelet aggregation assay. Specifically, collected platelets were split and single stained with two different antibodies, anti-CD31 and anti-CD42b. Upon stimulation with a cocktail of agonists (thrombin, ADP, epinephrine), we observed the appearance of a double-colored population with respect to unstimulated control (FIG. 7E). All together, these data demonstrated the physiologically-relevant morphological and functional properties of the platelets produced by the 3D silk tissue perfusion system.

Figure 8:
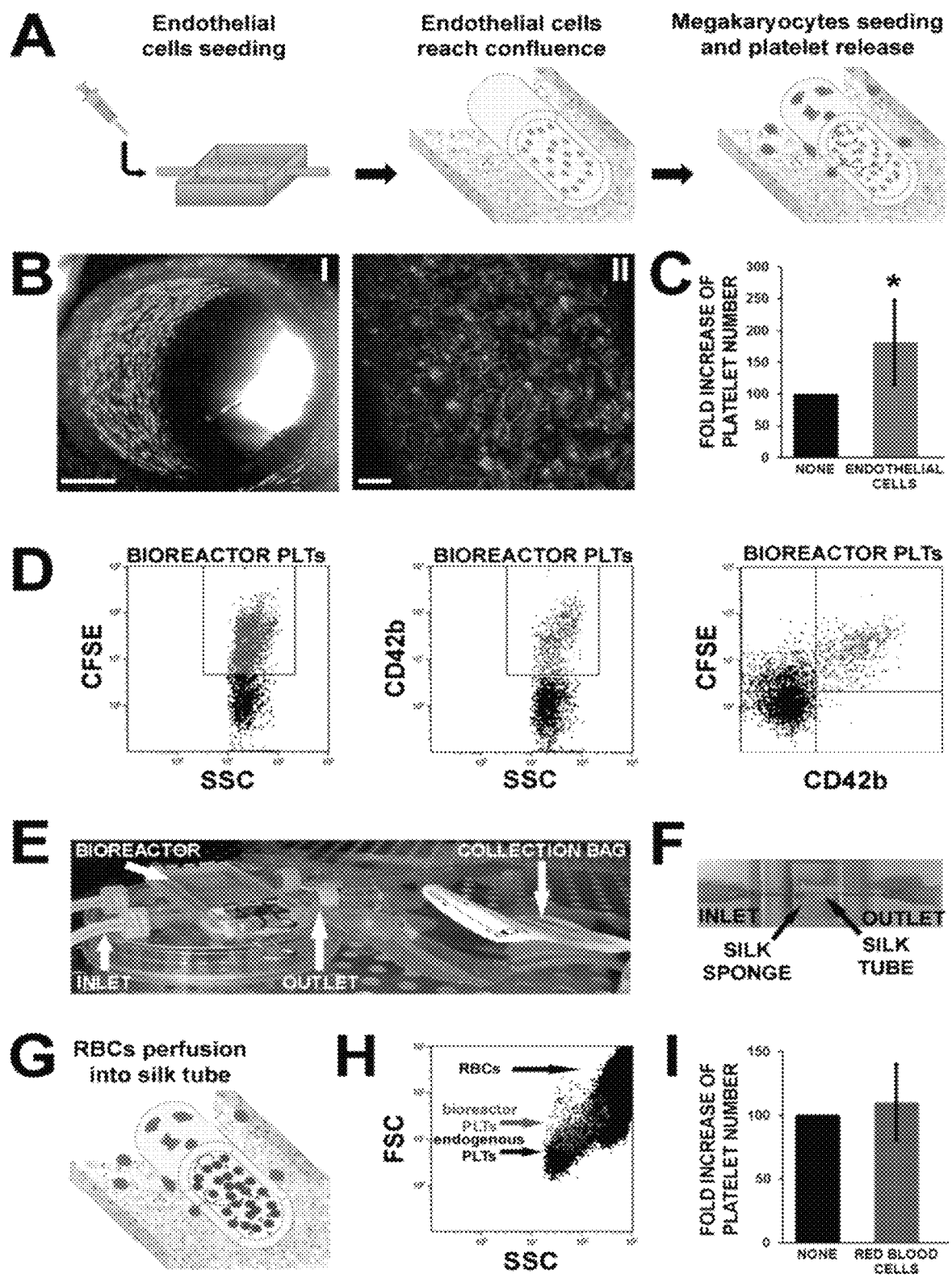
FIG. 8A-I shows, among other things, that adding endothelial cells to the porous silk membrane/tubes and red blood cells to perfusate improved platelet production and function. Specifically, panel A shows an exemplary schematic of a silk tube lumen supported a confluent monolayer of human dermal microvascular endothelial cells (in this Example, HMVEC-d). Panel B I shows exemplary confocal microscopy images of confluent HMVEC-d in the silk tube lumen (green=VE-cadherin; scale bar=100 µM). Panel B II shows a magnification of HMVEC-d seeded into silk tube lumen (green=VE-cadherin; blue=nuclei; scale bar=50 µM). Panel C shows an exemplary graph of a statistical analysis of collected platelets after perfusion of endothelialized silk tube with respect silk tube without HMVEC-d as compared to a silk tube with no endothelial cells (*p<0.05). Panel D shows collected platelets derived from CFSE labeled Mks seeded into bioreactors and perfused displayed positive staining for both CFSE and CD42b by flow cytometry analysis. Panels E and F shows exemplary photographs of a provided composition/system designed to mimic aspects of blood perfusion within the model tissue system, the silk vascular silk tubes were embedded into silk sponges and perfused with a suspension of 5% erythrocytes. Panel G shows a schematic of an exemplary provided method wherein, prior to seeding, the Mks were stained with CFSE and the released platelets were analyzed as CFSE and CD42b positive cells. Panel H shows exemplary flow cytometry data showing that $CFSE^+CD42b^+$ platelets were distinguishable from endogenous platelets and red blood cells. Panel I shows an exemplary graph of the fold increase in collected platelets while being perfused with red blood cells, which was not statistically different compared to the media-only control in this Example.

To further mimic the composition of the vascular niche, human dermal microvascular endothelial cells (HMVEC-d) were cultured within the silk tube lumen prior to seeding $2.5 \times 10^5$ Mks into the silk sponge (FIG. 8A). Co-cultures with endothelial cells have been used for the in vitro vascularization of a variety of tissues, including bone and adipose, where endothelial cells were introduced into tissues via 3D multicellular spheroids or simple mixing of cultures. Here, endothelial cells were seeded directly into the functionalized silk tube lumens. After one week of culture, the endothelial cells formed a confluent layer covering the inner wall of the silk tubes and exhibited characteristic cobblestone morphology and VE-cadherin staining that localized to the cell-cell junctions (FIG. 8B I, II). Endothelialized vascular tubes exhibited a significant increase in the number of collected platelets compared to non-endothelialized silk vascular tubes (FIG. 8C).

To assess platelet release by in vitro differentiated human Mks, the cells were stained with 0.5 µM carboxyfluorescein diacetate succinimidyl ester (CFSE) fluorescent cell staining dye and then seeded in the silk sponges as described above. Released platelets were counted as CFSE and CD42b positive cells (FIG. 8D). To study the effect of blood cell perfusion on Mk platelet production, the silk vascular tubes were perfused with erythrocytes resuspended in culture medium at 5% of hematocrit (FIG. 8E, F, G). The erythrocyte suspension was constantly agitated and perfused into the bioreactor using a peristaltic pump at a shear rate of 60/s. The number of $CFSE^+CD42b^+$ platelets produced in vitro was not significantly increased from the control condition in which tubes were perfused with only media (FIG. 8I). These experiments demonstrate that while perfusion of red blood cells through the 3D silk tissue does not improve in vitro platelet production it can presumably be used to modulate oxygen tension in the bioreactor by applying a flux of erythrocytes able to manipulate oxygen delivery and release in the vascular niche, as well as to provide reactive oxygen species scavenger agents in the osteoblastic and vascular niches.

In conclusion, this Example describes a physiologically relevant, 3D human tissue model of the bone marrow and vascular niche that is capable of generating functional platelets in vitro, with endothelial cell co-cultures supporting significantly increased numbers. The model presented in this Example also offers a simple method for the incorporation of labile compounds to study the role of biochemical factors on platelet outcomes, without loss of bioactivity. The tunability of silk enables a wide range of material formats that can be integrated to reproduce a niche-like bone marrow microenvironment. Importantly, the low thrombogenicity, non-toxicity and low-immunogenicity of silk provides a unique and versatile system for tissue regeneration. Furthermore, we were able to reproduce and visualize, in vitro, the extension of proplatelet-like protrusions into micro-vessels that has been shown in vivo. The physiologically relevant structure and composition of the silk tubes were achieved by gel spinning and functionalization of the silk tubes with different ECM components and SDF1-α, as well as by the presence of the endothelial cells lining the inner wall of the tubes. Blood flow was mimicked by perfusion of reconstituted red blood cells while the bone marrow environment structure was obtained by embedding the vascular tube into silk sponges. The approach is very efficient as millions of functional human platelets are generated from a low number of Mks, establishing feasibility towards clinically relevant production systems for future directions in platelet supplies as well as in the study of platelet-related diseases. According to various embodiments, this system may also be implemented with the use of human induced pluripotent stem cells (iPSC) and/or embryonic stem cells (ESCs) for generation of functional platelets to be transfused. Overall, this 3D bone marrow tissue perfusion system provides a versatile tool for studying platelet production in vitro offering additional opportunities in the identification of new therapeutic targets while avoiding the need for animal models.

Example 3

Silk Based System for the Generation of Blood Components Ex Vivo

As described herein, there is a critical need for bioengineering models that reflect key features of the physiological bone marrow environment for functional blood cell generation ex vivo. Provided systems, including those described in this Example, may provide mechanistic understanding and control of hematopoiesis as well as systems for therapeutic utility such as for the ex vivo screening of therapeutic compounds.

As also described elsewhere herein, blood cells are produced by the red bone marrow that is normally contained in spongy bones. The bone marrow supports hematopoietic stem cell self-renewal as well as differentiation into committed lineages in order to support the physiologic homeostasis of blood cells. Bone marrow failure may result from diseases, trauma, or cancer treatments, among other causes, leading to a decreased production of blood cells and the consequence of necessity for blood transfusions. Hematopoiesis is regulated by specialized cells (i.e. endothelial cells), soluble factors (i.e., cytokines) and components of the extracellular matrix (ECM) that together constitute the hematopoietic 'niche' or microenvironment. The venous sinusoids are the site of the passage of mature blood cells between the bone marrow compartment and the blood stream. The walls of the sinusoids consist solely of a layer of endothelial cells on a discontinuous basement membrane. Basement membranes are widely distributed ECM components that coat the basal aspect of endothelial cells and play a role in maintaining tissue and organ function in the adult. Mutations adversely affecting expression of the different structural components are associated with diseases of different organs such as brain, vasculature and kidney. The importance of ECM components in the maintenance of correct hematopoiesis is clear as demonstrated by the alteration of this process observed in tenascin and collagen type X knock-out mice. However, the mechanisms by which the bone marrow vascular niche, namely the ECM components and vascular endothelium, coordinate blood cell production are not completely known both in normal and disease conditions.

In the bone marrow, platelets are generated by megakaryocytes (Mks) that associate with the bone marrow vasculature where they convert their cytoplasm into proplatelets that protrude through the vascular endothelium into the lumen and release platelets. Endothelial cells were shown to be key regulators of platelet production. Moreover, individual ECM components were demonstrated to play a role in the regulation of Mk development in vitro. Fibronectin was shown to regulate Mk maturation and proplatelet extension, while type III and type IV collagens supported proplatelet formation in vitro. In contrast, type I collagen is an important physiological inhibitor of platelet release in vitro.

In this Example, an ex vivo three-dimensional (3D) tissue model of the bone marrow microvascular niche was developed. One unique aspect to the compositions/systems exemplified in this Example was utilization of silk protein biomaterial in order to avoid activation of the cells, thus, allowing direct control over system functions and differentiation based on the growth factors provided and not due to any biomaterial surface activation. As discussed elsewhere herein, silk is a biologically-derived protein polymer that has useful properties for tissue engineering, including biocompatibility, robust mechanical strength, slow and controlled degradation into nontoxic products in vivo and non-thrombogenic features. Silk can be prepared in a range of material formats, including films, hydrogels and microspheres. Finally, silk can be processed entirely in aqueous systems using mild, ambient conditions of temperature and pressure, allowing the incorporation of labile compounds without loss of bioactivity. Using human-derived cells, a bone marrow niche tissue model was developed in which Mk function and platelet generation were measured in response to changes in ECM component silk functionalization, surface topography, stiffness and co-culture with endothelial cells. Additionally, experiments were performed under perfusion culture in which the membrane model was adapted into a hollow tube embedded in a silk sponge, to mimic bone marrow structure. The system was connected to a perfusion bioreactor and the results show, inter alia, that substrate composition, ultrastructure and stiffness, as well as endothelial cell co-culture and perfusion, were key factors affecting ex vivo platelet production.

Methods

Unless otherwise stated, the methods, reagents and processes used in this Example were as follows:

Materials

*Bombyx mori* silkworm cocoons were supplied by Tajima Shoji Co., Ltd. (Yokohama, Japan). Stainless steel wire, Type 304V, was supplied by Small Parts (Miami Lakes, Fla., USA). Pharmed tubing was from Cole-Parmer (Vernon Hills, Ill., USA). Transfer bags for platelet collection were from Fenwal (Mont Saint Guibert, Belgium). Human fibronectin, laminin from human fibroblast and Type IV collagen from human placenta were from Sigma (Saint Louis, Mo., USA). Fibrinogen from human plasma was from Calbiochem (Spring Valley, Calif., USA). Type I collagen was purified as described previously. Immunomagnetic separation system was from Miltenyi Biotech (Bergisch Gladbach, Germany). Recombinant human thrombopoietin (TPO), interleukin 6 (IL-6), interleukin 11 (IL-11), and Stromal Derived Factor (SDF)-1α were from Peprotech (London, UK). 5-(and 6)-Carboxyfluorescein diacetate succinimidyl ester (CFSE) was from BioLegend (London, UK). TruCount tubes and PAC-1 FITC were from Becton Dickinson (S. Jose, Calif., USA). The following antibodies were used: mouse monoclonal anti-CD61, clone SZ21, from Immunotech (Marseille, France); rabbit monoclonal anti-β-tubulin was a kind gift of Prof. Joseph Italiano (Brigham and Women's Hospital, Boston, USA), mouse monoclonal anti-α-tubulin (clone DM1A) (Sigma-Aldrich, S. Louis, Mo., USA); goat polyclonal anti-CD61 (clone C-20) (Santa Cruz Biotechnology, Calif., USA); PE mouse monoclonal anti-human CD42b (clone HIP1), FITC mouse monoclonal anti-human CD61 (clone PM6/13) and FITC polyclonal anti-human CD31 were from Abcam (Cambridge, UK); rabbit polyclonal anti-VE-Cadherin was from Thermo Scientific (Rockford, Ill., USA); Alexa Fluor 488-conjugated antibodies and Hoechst 33258 were from Life Technologies (Carlsbad, Calif., USA).

Cell Cultures

Human umbilical cord blood was collected following normal pregnancies and deliveries upon informed consent of the parents, in accordance with the ethical committee of the IRCCS Policlinico San Matteo Foundation and the principles of the Declaration of Helsinki. Megakaryocytes (Mks) were differentiated from human umbilical cord blood-derived CD34$^+$ cells using previously described methods. Briefly, CD34$^+$ cells were separated by an immunomagnetic beads technique and cultured for 13 days in Stem Span media (STEMCELL Technologies, Vancouver, Canada) supplemented with 10 ng/mL TPO, IL-6, and IL-11, and 1% penicillin-streptomycin. Media was changed every 3 days.

Endothelial progenitor cells (EPCs) were differentiated from human umbilical cord blood-derived CD34$^+$ cells using a previously described method. Briefly, CD34$^+$ cells were plated in EGM2-MV media (Lonza, Basel, Switzerland) in type I collagen-coated dishes (BD Biosciences) at an approximate density of $10 \times 10^3$ cells/cm$^2$. Non-adherent cells were removed after 36-48 hours. The media was changed every 2-3 days for four weeks until colonies reached confluence. Cells were trypsinized and expanded in flasks coated with type I collagen (rat tail, BD Biosciences). Human dermal microvascular endothelial cells (HMVEC-d) (P3-6) were purchased from Lonza and cultured in Endothelial Cell Growth Media-2, EGM 2-MV supplements and 5% fetal bovine serum (Lonza). The media was changed every 2-3 days.

Silk Solution Preparation

Silk fibroin aqueous solution was obtained from *Bombyx mori* silkworm cocoons according to previously published literature. Briefly, *Bombyx mori* cocoons were de-wormed and chopped. The chopped cocoons were boiled for 10 minutes in 0.02 M Na$_2$CO$_3$ solution at a weight to volume ratio of 5 g to 2 L. The fibers were rinsed for 20 minutes for three times in distilled water and dried overnight. The dried fibers were solubilized for 4 hours at 60° C. in 9.3 M LiBr at a weight to volume ratio of 3 g to 12 mL. The solubilized silk solution was dialyzed against distilled water using a Slide-A-Lyzer cassette (Thermo Scientific, Waltham, Mass., USA) with a 3,500 MW cutoff for three days and changing the water a total of eight times. The silk solution was centrifuged at 3,220 g for 10 minutes to remove large particulates and stored at 4° C. The concentration of the silk solution was determined by drying a known volume of the solution and massing the remaining solids.

Silk Membrane/Film Fabrication

Silk solution (1% w/v) containing polyethylene oxide (PEO) porogen (0.05% w/v; 900,000 MW, Sigma) was cast on polydimethylsiloxane (PDMS; Dow Corning) molds (45 µL cm$^{-2}$ of mold surface area) and dried at 22° C. for 16 hours. ECM components were added to the silk film, either immobilized within the silk film or adsorbed to the film surface. Entrapped ECM silk films were prepared by mixing the ECM components with the silk prior to casting. ECM components were mixed to the 1% silk solution with 0.05% PEO and sonicated for 5 minutes in an ultrasound bath to ensure proper mixing of all the components and right pore formation. Adsorbed ECM silk films were incubated with the ECM components overnight at 4° C. The following ECM components were used: 25 µg mL$^{-1}$ fibronectin (human plasma, BD Biosciences), 25 µg mL$^{-1}$ collagen type I (human, Sigma), 25 µg mL$^{-1}$, laminin (human, Sigma), 100 µg mL$^{-1}$ fibrinogen (human, Calbiochem). Silk films were water annealed in a vacuum chamber containing 100 mL of water at the bottom of chamber. The water annealing chamber was maintained at either 60° for 16 h or 22° C. for 16 hours or 4° C. for 6 to achieve "High", "medium" and "low" silk film mechanical properties, respectively. Silk films were lifted off the PDMS mold and exposed to ultraviolet light for 30 minutes per side inside of a sterile biological hood. For co-culture experiments, the membrane from Transwell inserts (Corning) was removed under sterile conditions using a 5 mm biopsy punch. Silk films were trimmed using an 8 mm diameter biopsy punch and secured to the Transwell insert using a sterile, medical-grade silicon glue (Dow Corning). The films were rinsed three times in PBS overnight at 4° C. For experiments not performed in Transwell inserts, films were secured between two rings of scotch tape (6 mm inner diameter, 12 mm outer diameter) according to previously described methods, which assisted in handling of the sample. To prevent the films from floating during cell culture, films were secured to the bottom of 24-well plates using silicon rings (10 mm inner diameter, 15.5 mm outer diameter, McMaster Carr). All samples were sterilely washed three times in PBS over the course of 24 hours to remove the PEO porogen. Prior to cell seeding, silk films were soaked in cell culture media for one hour.

Elastic Modulus Determination

Elastic modulus maps were taken on an Asylum Research MFP-3D Atomic Force Microscope (AFM) (Asylum Research, Santa Barbara, Calif.) using AC240TS-R3 cantilevers (Asylum Research, Santa Barbara, Calif.) with a nominal spring constant of 2 N/m. Films were hydrated with Dulbecco's Phosphate Buffered Saline (Life Technologies, Grand Island, N.Y.) and a minimum of 300 AFM force vs. indentation curves were taken in the fluid solution on each film. Cantilevers were calibrated in air and in the buffer solution prior to measurement to determine accurate spring constant values. Elastic modulus values were determined using the inbuilt Hertz Model fitting function of the Asylum Research MFP3D software.

Evaluation of Mk Adhesion and Proplatelet Formation

In order to analyze megakaryocyte adhesion and proplatelet formation onto different extracellular matrix components, 12 mm glass cover-slips or silk films were coated with 25 µg/ml type I collagen, 100 µg/ml fibrinogen, 25 µg/ml fibronectin, 25 µg/ml type IV collagen or 25 µg/ml laminin, overnight at 4° C. At day 13 of culture Mks were harvested and allowed to adhere at 37° C. and 5% CO$^2$. After 16 hours samples were fixed and stained for the microscopy analysis, as subsequently described.

Megakaryocytes-Endothelial Cell Co-Culture

We removed the polycarbonate membrane from a Transwell insert and pasted the silk film membrane to the insert using a biocompatible silicon-based adhesive. Mks were seeded at an approximate density of $2.5 \times 10^5$ cells/cm$^2$ in Stem Span media supplemented with 10 ng/mL TPO, and 1% penicillin-streptomycin. Endothelial cells were seeded at an approximate density of $7 \times 10^4$ cells/cm$^2$ in EGM2-MV media. EPCs were allowed to attach for two hours before flipping the Transwell insert right side up into a 24-well culture plate. EPCs were cultured for 24-36 hours until confluence was reached before seeding Mks in the upper chamber of the Transwell insert after which the media used was Stem Span supplemented with TPO and 1% penicillin-streptomycin and 300 ng/ml SDF-1.

Preparation of Gel-Spun Membranes/Microtubes

Porous silk tubes were fabricated by gel spinning aqueous silk solutions around small diameter wires according to previously reported methods. Briefly, 15% aqueous silk solution produced by degumming *Bombyx mori* silkworm cocoons for 10 minutes was mixed with the extracellular matrix proteins, fibronectin, type IV collagen and laminin to a final concentration of 50 µg mL$^{-1}$, and with 300 ng/ml SDF-la. Pores were obtained by adding 6 w/t % polyethylene oxide (PEO) to the silk fibroin to a volume ratio of 10:1 silk:PEO. The solution was loaded into a syringe capped with a 30 G needle and then extruded onto a polytetrafluoroethylene (PTFE)-coated stainless steel wire that was rotating at a rate of 200 RPM. Axial slew rate and rotations per minute were optimized to generate evenly distributed, continuous, and sturdy scaffolds. The microtubes were stored at −20° C. for 24 hours and then lyophilized on a semi-automatic cycle. Microtubes were subjected to a 60-minute methanol wash in order to transform silks amorphous structure into its β-form silk fibroin conformation characterized by anti-parallel β-sheets. Scaffolds were soaked in deionized water on a shaker plate for approximately 24 hours to leach out the PEO porogen and stored in deionized water at 4°.

Functionalized silk tubes presented 50±20 µm wall thickness with defined pore sizes of 22±4 µm. Before any cell-based experiments, the microtubes were sterilized in 70% ethanol for at least 2 hours.

Perfusion Bioreactor Design

The previously reported bioreactor platform was adapted to re-create the characteristic features of the bone marrow environment such as osteoblastic and vascular niche. Bioreactors consist of two wells (15×20×5 mm) within a PDMS block (35×80×5 mm), which was plasma bonded to cover glass (Goldseal, No. 1, 24×60 mm; Ted Pella, Redding, Calif.). Stainless steel needles (23 G, blunt-ended) were positioned on either side of the bioreactor chambers, 50 µm from the bottom edge of the bioreactor and were connected to a perfusion system. The perfusion system was composed of a syringe pump (Harvard Apparatus) connected to the bioreactor inlet and a blood collection bag containing acid-citrate-dextrose (ACD) connected to the bioreactor outlet.

Silk Matrix/Sponge Preparation and Bioreactor Assembly

Functionalized silk membranes/tubes were trimmed to approximately 1.5 cm in length and secured over the blunt end needles within the perfusion bioreactor chamber. A porous silk matrix/sponge was then assembled around the tube using a salt-leaching process. Specifically, a 6% aqueous silk solution was dispensed around the tube and then NaCl particles (approximately 500 µm in diameter) were sifted into the silk solution in a ratio of 1 mL of 6% silk solution to 2 g of NaCl particles. The tubes and scaffolds were placed at room temperature for 48 hours and then soaked in distilled water for 48 hours to leech the NaCl particles. Scaffolds were trimmed to 5 mm in width and sterilized in 70% ethanol for 24 hours. Scaffolds were rinsed five times in phosphate-buffered saline (PBS) over 24 at 4°. At day 13 of Mk differentiation, $2.5 \times 10^5$ Mks were seeded into the silk sponge surrounding the tube for 24 hours. In some experiments before Mks seeding HMVEC-d were dispensed into the silk tube lumen at a cell density of $5 \times 10^6$ cells/mL. Tubes loaded with HMVEC-d cell suspension were incubated at 5% $CO_2$ and 37° C. for 2 hours, and then were flipped over and incubated for another 2 hours. During the incubation, a small amount of culture medium was supplied to the tubes to keep them moisturized. Samples were cultured statically for seven days to allow cells to proliferate and grow to confluence along the inner tube wall. Alternatively, the same method was applied to culture EPCs derived from umbilical cord blood in the silk tubes. After Mks seeding, the bioreactor chambers were sealed with a glass slide and the outlet ports were connected to the outlet needles. Culture media-filled syringes and tubing were connected to the inlet needles. The bioreactor was placed into the incubator (37° C. and 5% $CO_2$) and transfer bags for platelet collection containing acid-citrate-dextrose (ACD) were secured to the outlet ports. The syringes were placed into a syringe pump (Harvard Apparatus) located outside the bioreactor and media was pumped at 94 µL min$^{-1}$ for 6 hours.

Functionalized silk tube and sponge structure were analyzed using Zeiss EVO MA10 scanning electron microscope (SEM) (Carl Zeiss, Oberkochen, Germany). The scaffolds were coated with platinum/palladium for 60 seconds before SEM observation. Image analysis software (ImageJ, National Institutes of Health, USA) was used to measure the tube wall thickness and determine average pore size.

Immunofluorescence and Confocal Microscopy

For immunofluorescence imaging by confocal microscopy, silk membrane/film or silk matrices/sponges samples were fixed in 4% paraformaldehyde (PFA) for 20 minutes, permeabilized with 0.1% Triton X-100 (Sigma) for 5 minutes and then blocked with 5% bovine serum albumin (BSA, Sigma) for 30 minutes, at room temperature. Samples were probed with anti-CD61 (1:100), 1 hour at room temperature (silk film) or overnight at 4° C. (silk sponges), anti-α-tubulin (1:700) 1 hour at room temperature (silk film), or anti-β1-tubulin (1:1000) 1 hour at room temperature (silk film), and then immersed in Alexa Fluor secondary antibody (1:500) for 2 hours at room temperature. Nuclei were stained with Hoechst. Samples were imaged by a TCS SP2 confocal laser scanning microscope (Leica, Heidelberg, Germany) equipped with ×20 and ×63 oil-immersion objectives. Adherent- and proplatelet forming-Mks were determined by counting the number of cells expressing CD61 and/or β1-tubulin in eight fields of view using a 40× objective on a fluorescent microscope, as previously described. Confluent EPC or HMVEC-d within were incubated overnight with anti-human-VE-Cadherin (1:150) and immersed in Alexa Fluor-488 goat anti-rabbit secondary antibody (1:250). Samples were scanned using a Leica SP2 confocal microscope (Leica Microsystems, Buffalo Grove, Ill.) equipped with ×20 objective or a TCS SP2 confocal laser scanning microscope (Leica, Heidelberg, Germany) equipped with ×20 and ×63 oil-immersion objectives. Nuclei were stained with Hoechst or DAPI.

Whole Blood Collection and Peripheral Blood Platelets Isolation and Perfusion

Human whole blood was collected from healthy volunteers, in accordance with the ethical committee of the IRCCS Policlinico San Matteo Foundation and the principles of the Declaration of Helsinki, using citric acid-citrate-dextrose (ACD) as anticoagulant. Samples were perfused into functionalized silk tubes by a syringe pump (Harvard Apparatus) at 94 µL min$^{-1}$. Blood count before and after perfusion was performed with an ADVIA 2120 Hematology System. Human peripheral blood platelets were isolated from whole blood that was centrifuged at 150 g for 10 minutes to obtain platelet-rich plasma (PRP). PRP was then diluted with culture media and divided in two samples: one was perfused into functionalized silk tubes by a syringe pump (Harvard Apparatus) at 94 µL min$^{-1}$ and collected in an ACD-containing collection bag, the other was left to rest in an ACD-containing collection bags. Both were maintained at 37° C. and 5% $CO_2$. Physical parameters and functionality of peripheral blood platelets before and/or after perfusion were analyzed by flow cytometry, as subsequently described.

Analysis of Platelet Functionality

Physical parameters and functionality of peripheral blood and in vitro generated platelets were analyzed by flow cytometry. Collected platelets produced in vitro by basal membrane model or after perfusion of silk microtubes were analyzed using the same forward and side scatter pattern as human peripheral blood platelets after perfusion through the silk tubes. In vitro produced platelets were identified as $CD61^+CD42b^+$ and their number was calculated using a TruCount bead standard.

For the analysis of platelet functionality, in vitro produced platelets by perfusing silk microtubes or peripheral blood platelets after perfusion through functionalized silk tubes were centrifuged at 2500 g for 15 minutes. The pellet was gently resuspended in Tyrode's buffer (134 mM NaCl; 0.34 mM $Na_2HPO_4$; 2.9 mM KCl; 12 mM $NaHCO_3$; 20 mM HEPES; 5 mM glucose; 2.5 mM $Ca^{2+}$; 2.5 mM $Mg^{2+}$; pH 7.0) and allowed to rest for 1 hour at room temperature. Samples were activated with 3 U/ml thrombin, or 25 µM ADP, or 25 µM epinephrine (all from Sigma), for 15 minutes at 37° C. Unstimulated platelets were used to gate for non-activated platelets and stimulated peripheral blood platelets were used to gate for activated platelets. All samples were probed with FITC conjugated PAC-1. CD42+ events exhibiting PAC-1 binding were considered functional activated platelets. Importantly, PAC-1 binding was measured using the same fluorescence intensity of human peripheral blood platelets.

For the analysis of platelet aggregation we performed a flow cytometry-based aggregation assay. Briefly, in vitro produced platelets were separately labeled with anti-CD31 or anti CD42b for 15 minutes at room temperature. After incubation, samples were centrifuged 15 minutes at 2500 g, resuspended in Tyrode's buffer and allowed to rest for 1 hour at room temperature. Then, the 2 populations of differently labeled platelets were mixed 1:1 and incubated in the presence or absence of a cocktail of agonists containing 3 U/ml thrombin, or 25 µM ADP, or 25 µM epinephrine. Double-colored events were considered aggregated platelets. All samples were acquired with a Beckman Coulter Navios flow cytometer. Off-line data analysis was performed using Beckman Coulter Navios software package.

Human Red Blood Cell Isolation and Perfusion

Human whole blood was collected from healthy volunteers into heparinized tubes in accordance with the ethical committee of the IRCCS Policlinico San Matteo Foundation and the principles of the Declaration of Helsinki. Red blood cells were isolated by centrifugation at 1400 g at 4° C. for 10 minutes from freshly drawn blood. The serum and buffycoat were removed and the packed cells were washed 10 times with Hepes buffer (10 mM Hepes, 154 mM NaCl, 5 mM glucose, pH 7.4) and resuspended in culture media at a 5% hematocrit. The erythrocyte suspension was transferred to a transfer bag that was constantly agitated during perfusion. Red blood cells were perfused through the tube at a rate of 94 µL min$^{-1}$. Parallely, a bioreactor was perfused with media only, as described above. In these experiments, to differentiate between peripheral blood platelets and in vitro produced platelets, prior to seeding, in vitro differentiated Mks were labeled with 0.5 µM CFSE for 15 minutes at room temperature. Mks were then washed 2 times with culture media and finally seeded into silk sponge, as described above. Collected platelets were analyzed by flow cytometry and counted as CFSE+CD42b+ events.

Statistics

Values were expressed as mean plus or minus the standard deviation (mean±SD). Student's t-test was performed for paired observations. A value of $p<0.05$ was considered statistically significant. All experiments were independently replicated at least three times.

Results

Figure 10:
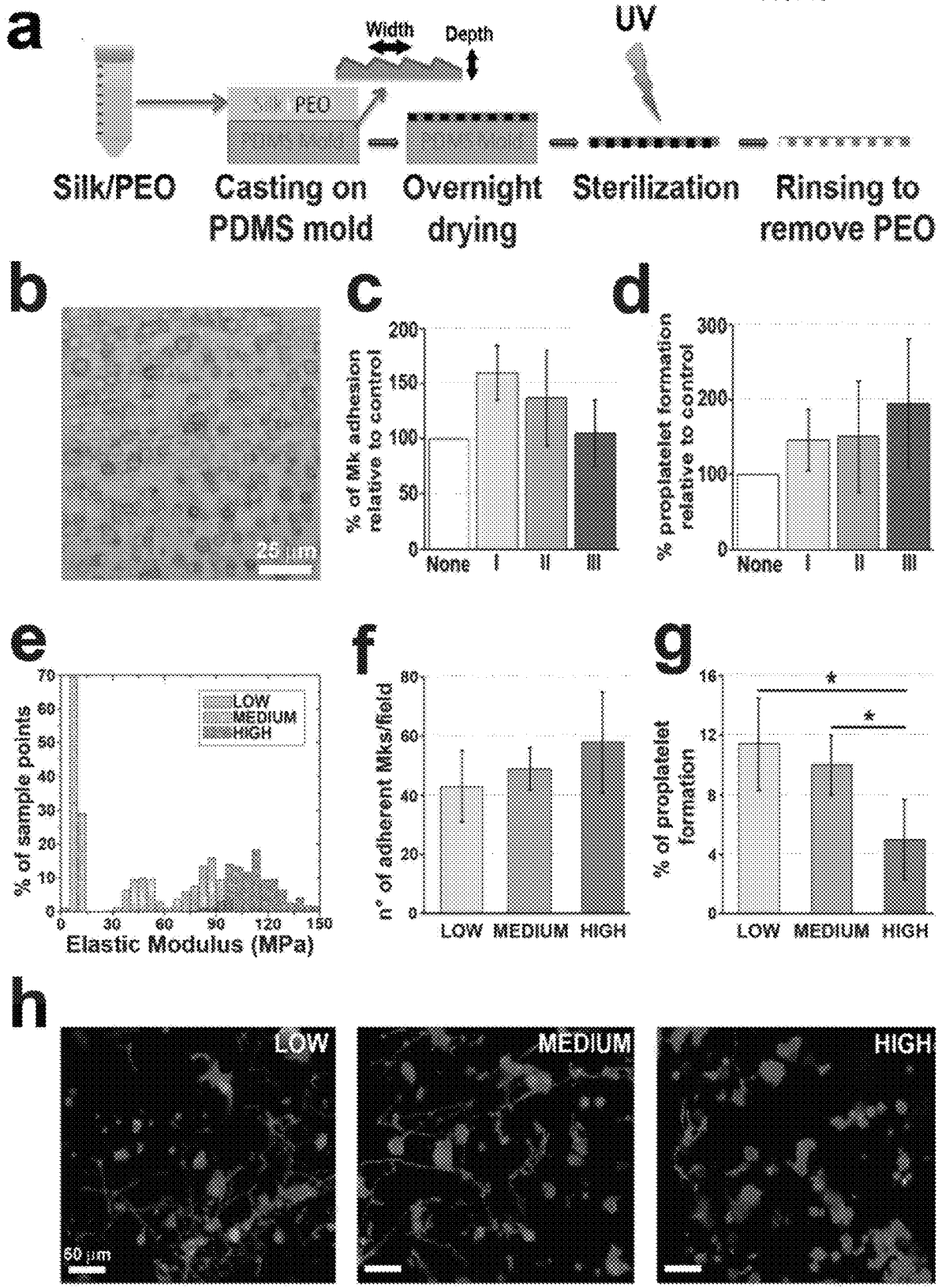
FIG. 10A-H. Effect of silk film topography and stiffness on megakaryocyte adhesion and proplatelet formation. (A)

In this Example, porous silk membranes/films were fabricated as previously described by casting a silk film solution containing a PEO porogen onto a PDMS mold. The solution was let air dry overnight and the resulting film water-annealed to induce β-sheets formation (FIG. 10a). The amount of silk protein cast onto the PDMS mold was chosen to obtain a 2-4 µm thick film and the ratio of PEO porogen to silk protein was set to obtain pores that transcended through the thickness of the film (FIG. 10b). The silk film surface topography was determined by changing the surface pattern on the PDMS mold (FIG. 10a). The features on this mold could be precisely controlled down to tens of nanometers and transferred to the silk film with minimal variability; the characteristics of the patterns used are reported in Table 1. Cord blood derived Mks were seeded onto coated silk films to assess cell adhesion and percentage of proplatelets forming cells.

TABLE 1

Spatial Parameters of Exemplary Surface Patterns

| Pattern | Depth (nm ± SD) | Width (nm ± SD) | Roughness (nm ± SD) |
|---|---|---|---|
| None | — | — | 3.2 ± 0.5 |
| I | 39 ± 5.3 | 445 ± 33 | 11.6 ± 1.6 |
| II | 64 ± 4.1 | 1796 ± 173 | 19.5 ± 1.3 |
| III | 465 ± 55 | 1898 ± 113 | 156.7 ± 13.8 |

As shown in FIG. 10c, surface topography significantly affected Mk adhesion as compared to unpatterned silk films. Indeed, Pattern I with depth and width features less than 500 µm improved Mk adhesion compared to the unpatterned silk films and to Pattern III, which had depth and width features that exceeded 500 µm and a roughness value ~10× that of Pattern I. In contrast, no significant differences in proplatelet formation were observed on the different patterns (FIG. 10d). Therefore, Pattern I, was chosen as processing conditions to maximize Mk adhesion for further characterization. It's widely accepted that the soft gelatinous ECM typical of the vascular niche promotes proplatelets formation and cell migration, while the stiff collagen I rich endosteal surface prevents the premature formation of proplatelets in the bone marrow space. On this basis we searched whether it was possible to reproduce some of this features in our system by varying the processing conditions of the silk films. Three different processing protocols were chosen to obtain the broadest range of conditions (hereinafter referred as to "Low", "Medium" and "High" protocols) and the elastic modulus was measured via AFM nano-indentation in DPBS solution (FIG. 10e). A minimum of 300 points were measured over each surface. The Low film yielded an average elastic modulus value of 90±2 MPa, the Medium film yielded an average of 69±20 MPa, and the High film yielded an average of 113±16 MPa. These data demonstrate that one may easily obtain a wide range of physiological stiffness by simply varying β-sheets formation rate of silk films. As shown in FIG. 10f silk film stiffness did not significantly affect Mk adhesion, but did affect the percent of Mks that extended proplatelets, with the "low" and "medium" stiffness silk films supported significantly higher percent of proplatelets compared to the "high" stiffness sample (FIG. 10g). Representative fluorescent images show that the "low" and "medium" stiffness silk films supported the extension of long, branched proplatelets while on the "high" stiffness silk films proplatelets with decreased and shorter branching were observed (FIG. 10h). On this basis, medium stiffness was chosen as the optimum condition to maximize Mk adhesion and proplatelet formation for further characterization.

Figure 11:
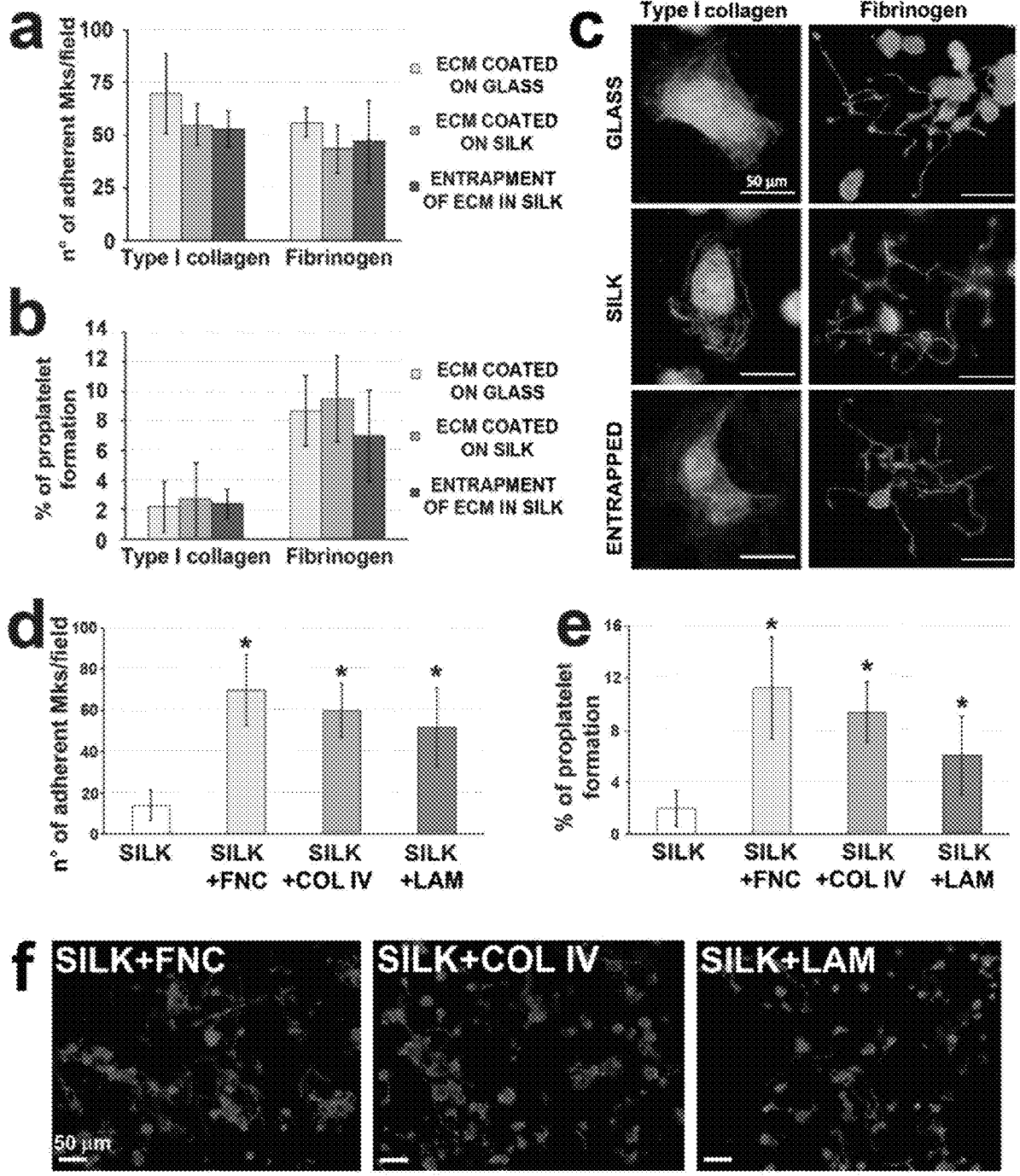

Silk can be functionalized, among other ways, by both absorption and entrapment with bioactive molecules. To test if different silk treatment could affect Mk behavior, silk films were functionalized by surface adsorption or entrapment with either collagen type I (COLI) or fibrinogen (FBG), which are substrates typically used to model Mk function. Regardless of the functionalization method, silk films sustain similar Mk adhesion and proplatelet formation as compared to glass coverslips coated with the same molecules (FIG. 11a-b). Further, Mk morphology was comparable in all the conditions (FIG. 11c). Most importantly, Mks sensed the ECM component entrapped in the silk film as demonstrated by the different behavior on COLI and FBG entrapped films. Specifically, sustained spreading and inhibition of proplatelet formation was observed on COLI entrapped silk films, while decreased spreading and proplatelet formation was observed on FBG entrapped films. Overall this data indicated that matrix proteins are stable inside silk films and maintain their biological activity on Mk function.

In order to model more physiological conditions, silk films were functionalized also with Fibronectin, Collagen IV and Laminin, that are the most represented ECM components around the bone marrow sinusoids. Functionalization with these ECM components significantly improved both Mk adhesion and proplatelet formation over the silk film only (FIG. 11d-e). In particular, the magnitude of proplatelet formation on type IV collagen (COL IV) and fibronectin (FNC) functionalized silk films had a trend towards increase as compared to laminin (LAM) treated silk films (FIG. 11e). Megakaryocyte morphology was similar between all functionalized silk films (FIG. 11f).

Figure 12:
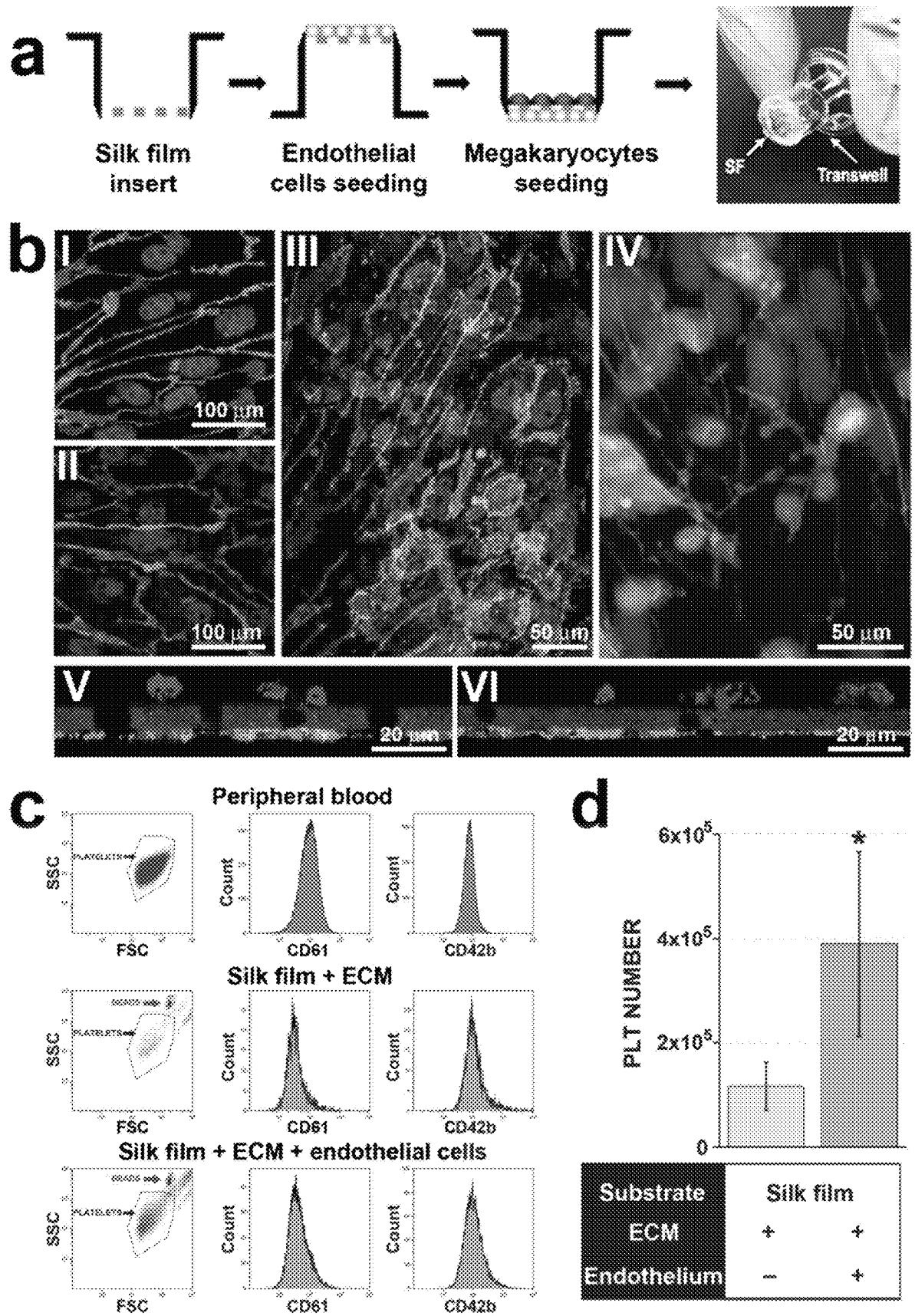

In the vascular niche Mks extend proplatelets inside the lumen of bone marrow sinusoids and release platelets in the circulation. Several factors contribute to this finely regulated process, among these cell-cell interactions and soluble factors are thought to play an important role, but the whole process is not fully understood. To study the role of endothelial cells in platelet release, functionalized silk films were mounted on plastic trans-wells after removing the original filter and secured using medical grade silicon glue. Endothelial primary cells (EPC) from cord blood were cultured on the bottom side of the silk films until confluent, and Mks seeded on the upper side (FIG. 12a) Immunofluorescence imaging showed similar endothelial cell cobble-stone morphology on the silk films compared to the glass (FIG. 12b I-II) and that co-cultures support both Mk adhesion (FIG. 12b III) and long, branched proplatelet formation (FIG. 12b IV). Confocal microscopy z-stack images showed that the Mks and endothelial cells remained localized to their respective side, separated by a porous silk film representing the discontinuous basement membrane present in the physiological bone marrow vascular niche (FIG. 12b V-VI). Mks/EPCs co-cultures or Mk alone on silk trans-wells were cultured in presence of the hematopoietic progenitor chemoattractor Stromal Derived Factor-1 (SDF-1-α) for 24 h and platelets were collected from the bottom chamber of the trans-well. Released platelets were analyzed by Flow Cytometry using peripheral blood platelets (PBPs) as a control. Platelet morphology and CD61/CD42b expression were comparable to peripheral blood controls both in Mk/EPCs co-culture and in functionalized silk film trans-wells without EPCs (FIG. 12c). Platelet numbers were determined by comparing the total number of platelet events to an internal counting standard using TruCount™ beads (FIG. 12c). As shown in FIG. 12d, Mk/EPCs co-culture determined an approximate 4-fold increase in platelet production compared to functionalized silk films alone. These results indicate that endothelial cells play an important role in the final stage of Mk development and in platelet release.

In order to mimic bone marrow microvasculature silk microtubes were fabricated using a gel spinning method and functionalized via entrapment of physiologically relevant ECM components (laminin, fibronectin, type IV collagen), and SDF-1α as chemoattractant. The resulting porous silk microtubes, that exhibited physiologically relevant wall thickness (50±20 μm) (FIG. 13a), were fitted into a bioreactor chamber. Functionalized tubes supported significantly higher Mk adhesion with respect to silk tubes without ECM components entrapment. Further, to mimic the bone marrow spongy architecture that surrounds the microvasculature and support hematopoietic progenitors function, we assembled a porous silk sponge, consisting of interconnected pores approximately 100-500 μm in diameter, around the functionalized silk microtubes (FIG. 13b). The biocompatible and non-thrombogenic properties of silk were demonstrated by perfusion of whole peripheral blood or a sample of washed platelets into the silk microtubes at shear rate of ~60/s. Complete blood count before and after perfusion demonstrated that hematopoietic parameters were not affected, demonstrating the absence of cell adhesion and/or activation to the silk vascular microtube inner wall under flow. Moreover, isolated platelets remained quiescent and maintained their capability of responding to physiological stimuli from thrombin and adenosine diphosphate (ADP) after passage through the functionalized microtubes, as demonstrated by PAC-1 binding. Additionally, no signs of clot formations were observed inside the silk vascular microtubes.

The ability of this new 3D tissue model to mimic physiologic bone marrow activity was proved by including into the silk sponge Mks, and by testing their ability to produce and release functional platelet into the microtube lumen, ex vivo. A total of $2.5 \times 10^5$ mature Mks, derived from umbilical cord blood hematopoietic progenitors, were seeded in silk sponges for 24 hours at 37° C. in a 5% $CO_2$ atmosphere (FIG. 14a) Immediately after seeding, Mks distributed homogeneously in the porous silk sponge (FIG. 14b I), and after 24 hours Mks were preferentially located around the outer wall of the silk vascular microtubes (FIG. 14b II). Further, Mks distributed along the external wall of the microtubes and elongated branched proplatelets across the microtube walls with platelet tips protruding into the microtube lumen (FIGS. 14b III-VII).

Figure 15:
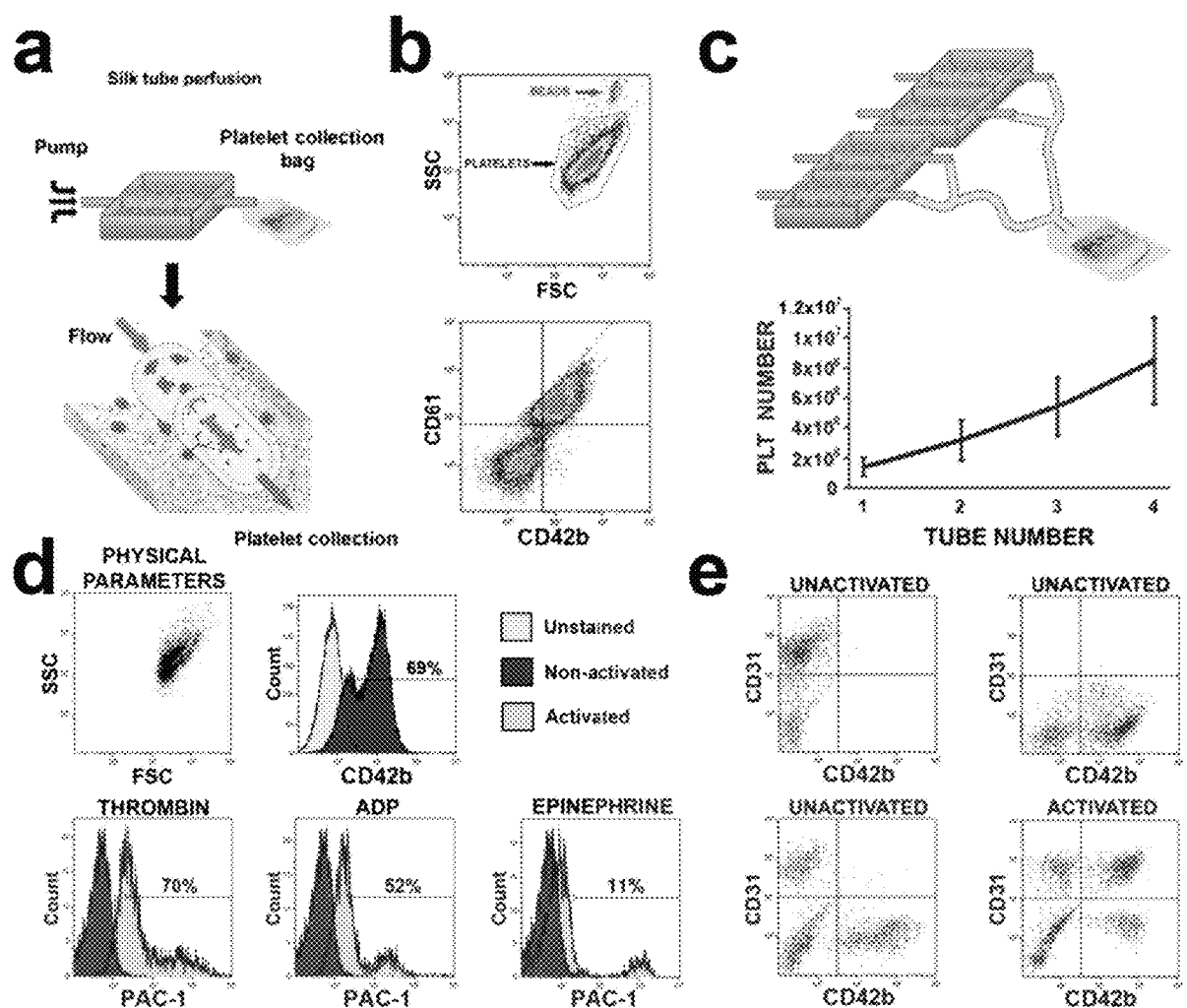

To mimic blood flow, the silk microtubes were perfused for 6 hours with culture medium using a syringe pump at 94 μL/min, corresponding to a shear rate of 60/s. The flow through of the vascular microtubes was collected into gas permeable-collection bags containing acid citrate dextrose (ACD) as anticoagulant (FIG. 15a). Collected platelets were double stained with anti-CD61 and anti-CD42b antibodies and exhibited similar physical parameters as human peripheral blood platelets, as determined by flow cytometry analysis (FIG. 15b). Importantly, the perfusate only contained platelets and was devoid of Mks. The number of $CD61^+$ $CD42b^+$ collected platelets was $1.4\pm0.6\times10^6$ per 3D tissue perfusion system and linearly increased with the use of multiple bioreactors in parallel (FIG. 15c). Collected platelets were determined to be functional based on increased PAC-1 binding to the activated integrin αIIbβ3 upon physiologic stimulation with both strong (i.e. thrombin) and weak (i.e. ADP, epinephrine) agonists (FIG. 15d). Platelet functionality was further confirmed by a flow cytometry-based platelet aggregation assay. Specifically, collected platelets were split and single stained with two different antibodies, anti-CD31 and anti-CD42b. Upon stimulation with a cocktail of agonists (thrombin, ADP, epinephrine), we observed the appearance of a double-colored population compared to the unstimulated control (FIG. 15e). All together, these data demonstrate that the exemplaified embodiments described herein are able to approximate physiologically-relevant morphological and functional properties of the platelets produced by the 3D silk tissue perfusion system.

Figure 16:
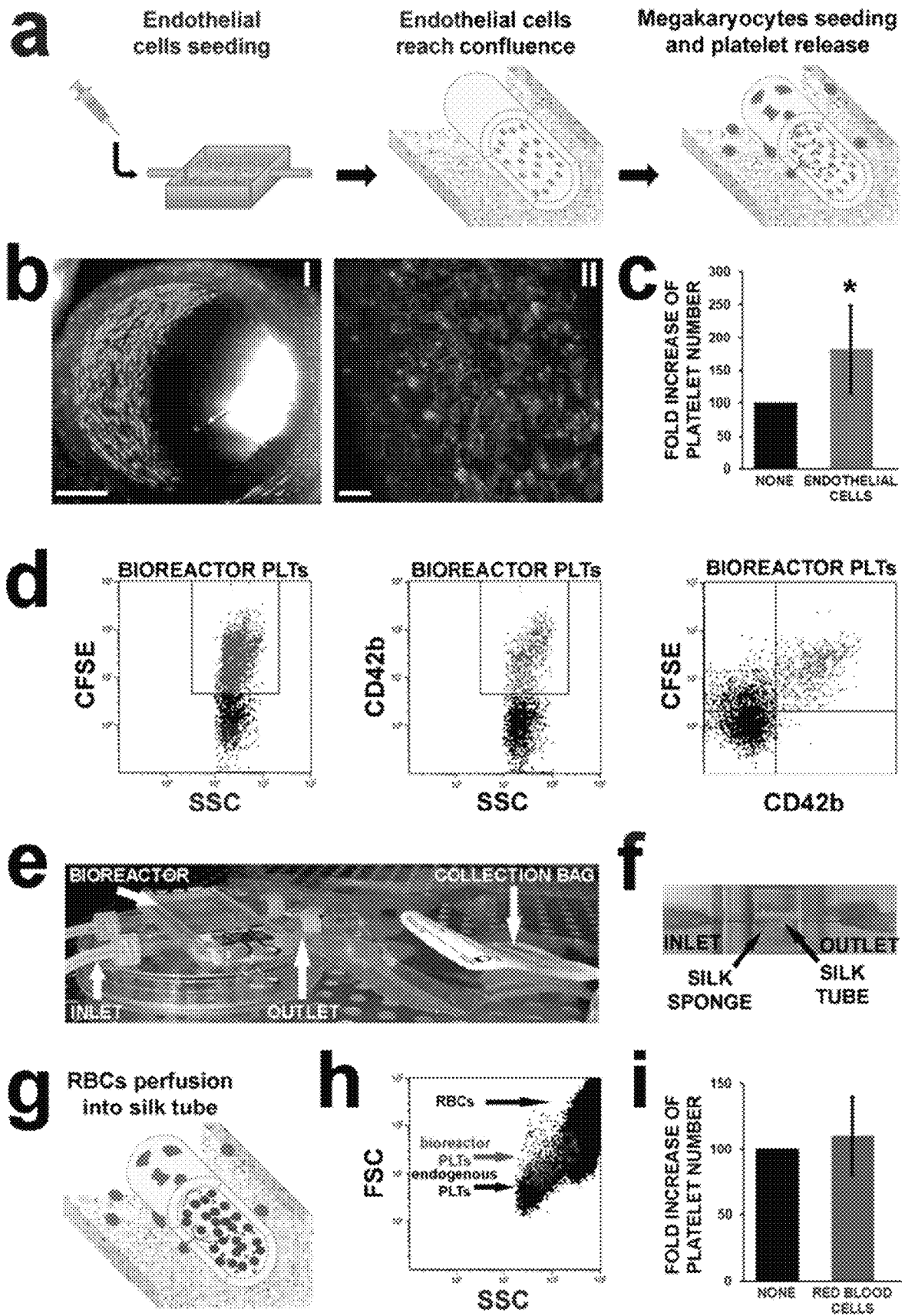

To further mimic the composition of the vascular niche, human dermal microvascular endothelial cells (HMVEC-d) or EPC were cultured within the silk microtube lumen prior to seeding 2.5×10 Mks into the silk sponge (FIG. 16a). Co-cultures with endothelial cells have been used for the in vitro vascularization of a variety of tissues, including bone and adipose, where endothelial cells were introduced into tissues via 3D multicellular spheroids or simple mixing of cultures. In this Example, endothelial cells were seeded directly into the functionalized silk microtube lumens. After one week of culture the endothelial cells formed a confluent layer covering the inner wall of the silk microtubes and exhibited characteristic cobblestone morphology and VE-cadherin staining that localized to the cell-cell junctions (FIGS. 16b I and II). Endothelialized vascular microtubes exhibited a significant increase in the number of collected platelets compared to non-endothelialized silk vascular microtubes (FIG. 16c). No differences were observed between the two endothelial cell sources (data not shown).

To study the effect of red blood cell perfusion on Mk platelet production, Mks were stained with 0.5 µM carboxyfluorescein diacetate succinimidyl ester (CFSE) cell staining dye, and then seeded in the silk sponges as described above. Silk vascular microtubes were perfused with erythrocytes resuspended in culture medium at 5% of hematocrit or culture media only. The erythrocyte suspension was constantly agitated and perfused into the bioreactor using a peristaltic pump at a shear rate of ~60/s. Released platelets were counted as $CFSE^+$ and $CD42b^+$ cells (FIG. 16d-h). The number of $CFSE^+CD42b^+$ platelets produced ex vivo was not significantly increased from the control condition in which microtubes were perfused with media only (FIG. 16i).

This Example describes the development of a bone marrow niche tissue model made from a porous silk membrane. The low surface activation of blood cells combined with the tunable properties of silk enables a wide range of material formats that can be integrated to reproduce a niche-like bone marrow microenvironment. Substrate topography and stiffness have both been shown to affect Mk adhesion and proplatelet formation. It was reported previously that Mks cultured on collagen type I had higher spreading and less proplatelet formation, while Mks cultured on N-acetylated collagen type I, which has lower stiffness and smaller fibrils than collagen type I, had lower spreading and higher proplatelet formation. We added to this work by decoupling the substrate topography and stiffness parameters and showed that surface topography preferentially influenced Mk adhesion while substrate stiffness preferentially influenced proplatelet formation. Interestingly, the surface topography did not appear to negatively impact proplatelet formation, which suggests that other factors are at play during adhesion-mediated proplatelet formation. In contrast, Mk adhesion was unaffected by substrate stiffness whereas proplatelet formation decreased with increasing substrate stiffness. Increasing stiffness also affected proplatelet morphology in terms of shaft length and branching.

One interesting feature of the model described in this Example is the ability to functionalize the silk by either surface adsorption or entrapment. When silk was functionalized with type I collagen and fibrinogen, the silk performed similarly to the coated glass cover slip controls. Also, there was no difference between Mk adhesion and proplatelet formation on functionalized silk films that had been coated or that had the ECM protein entrapped within the film as Mks were able to sense the ECM component entrapped in the silk membrane and behave consequently. Surface coating with bioactive molecules has several disadvantages, such as limited control on protein adsorption on the surface and rapid degradation. On the contrary, the advantage of entrapping the ECM components within the silk is that silk has been shown to stabilize bioactive molecules at physiologic conditions. This is a feature of the silk-based bone marrow model that can be leveraged if sensitive molecules such as ECM components or cytokines need to be incorporated into the model. Additionally, the thickness of ECM entrapped silk films can be adjusted to more closely mimic the bone marrow vascular niche physiology. Silk films were also functionalized with ECM components typically found around the bone marrow sinusoid in vivo. Specifically, entrapment of fibronectin, type IV collagen and laminin supported both Mk adhesion and proplatelet formation with a significant increase with respect to silk only.

Endothelial co-culture with Mks has shown that chemokines released by the endothelial cells may contribute to Mk maturation, Mk localization to the vascular niche, and increased platelet production. Additionally, Mk adhesion to endothelial cells is thought to increase Mk proliferation and maturation. Here we isolated and differentiated endothelial cells from human cord blood CD34+ cells and cultured them with Mks under experimental settings in which the two cell types were physically separated by the silk film. We confirmed the importance of Mks and endothelial cells co-culture by measuring a significant increase in platelet production in the co-culture conditions compared to the Mk-only cultures. These results suggest that the tunable features of the silk film model, namely ECM entrapment, surface topography, and stiffness, optimized with the concomitant presence of endothelial cells can support platelet production and release ex vivo. Shear forces and perfusion culture have been shown in the literature to have significant effects on proplatelet formation and platelet release. Therefore, we engineered a physiologically relevant, 3D human tissue model of the bone marrow and vascular niche capable of generating functional platelets ex vivo, with endothelial cells co-cultures significantly increasing the numbers of released platelets. Blood flow was mimicked by perfusion of reconstituted red blood cells while the bone marrow environment was obtained by embedding the vascular silk microtubes into porous silk sponges. This 3D model supported Mk migration to the tube and the porosity of the silk tube allowed Mks to extend proplatelets through the tube wall and to release platelets into the lumen space. Interestingly, perfusion of red blood cells through the 3D silk tissue did not improve ex vivo platelet production. However, the perfusion of red blood cells represent an important step in reproducing the physiological blood flow of the vascular bone marrow niche and offers the unique possibility of modulating oxygen tension in some embodiments by delivering a flux of engineered erythrocytes that manipulate oxygen delivery and are capable of providing reactive oxygen species scavenger agents to the bone marrow niches.

In conclusion, this Example describes a physiologically relevant, 3D human tissue model of the bone marrow and vascular niche capable of generating functional platelets ex vivo, with endothelial cell co-cultures supporting significantly increased numbers. The model may be prepared from silk in any of a variety of ranges of material formats that enable the effects of incorporation of ECM components and labile compounds, surface topography, substrate stiffness, endothelial cell co-culture, and perfusion culture on megakaryopoiesis to be studied in a physiologically relevant and holistic manner. Since some provided embodiments are based on human-derived cells, they may provide a powerful tool in predicting drug efficacy and safety for candidate therapeutics. Patient-derived Mks and endothelial cells, which can be derived from several depots throughout the body can be cultured in this model and used to design patient-specific drug administration regimes. Additionally, ex vivo generated platelets could be used as a source of growth factors for wound healing in regenerative medicine, including healing of recalcitrant ulcers and burns, and stimulation of osseous tissue regeneration in dentistry and maxillofacial plastic surgery.

EQUIVALENTS

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated, and encompass various alternatives, modifications, and equivalents, as will be appreciated by those of skill in the art. Moreover, the features of the particular examples and embodiments, may be used in any combination. The present invention therefore includes variations from the various examples and embodiments, described herein, as will be apparent to one of skill in the art.

The invention claimed is:

1. A composition comprising:
   a porous silk membrane between about 2 μm and 100 μm thick, inclusive, comprising at least one silk wall defining a lumen;
   at least one functionalizing agent selected from the group consisting of fibronectin, collagen type IV, collagen type VI, von Willebrand factor, laminin, and fibrinogen;
   stromal derived factor-1α; and
   a three dimensional silk matrix comprising pores, wherein the pores are interconnected and the pores have a diameter of between about 5 and 500 μm, inclusive,
   wherein the three dimensional silk matrix at least partially surrounds the porous silk membrane, and
   wherein the stromal derived factor-1α is associated with the porous silk membrane,
   wherein the composition is adapted to receive a plurality of megakaryocytes that, in use, produce differentiated and functional platelets.

2. The composition of claim 1, further comprising a plurality of endothelial cells located at least partially within the lumen.

3. The composition of claim 2, wherein the plurality of endothelial cells are selected from the group consisting of human dermal microvascular endothelial cells, human umbilical vein endothelial cells, and primary human endothelial cells.

4. The composition of claim 2, wherein the plurality of endothelial cells form a confluent layer.

5. The composition of claim 4, wherein the confluent layer of the plurality of endothelial cells exhibit a cobblestone morphology and/or VE-cadherin staining.

6. The composition of claim 1, further comprising the plurality of megakaryocytes located at least partially within the three dimensional silk matrix.

7. The composition of claim 6, further comprising culture media flowing through the composition at a flow rate of about 20 μL/minute to 250 μL/minute.

8. The composition of claim 6, wherein the plurality of megakaryocytes produce platelets in the lumen.

9. The composition of claim 8, wherein at least 70% of the platelets produced from the plurality of megakaryocytes express CD61.

10. The composition of claim 8, wherein the platelets produced from the plurality of megakaryocytes exhibit a similar morphology and CD41 positive staining as compared to platelets isolated from peripheral blood.

11. The composition of claim 8, wherein about 30 to 3000 fold more platelets are produced per seeded cell when in the presence of endothelial cells as compared to a seeded cell not in the presence of endothelial cells.

12. The composition of claim 8, wherein the composition is characterized as being able to produce about $0.8 \times 10^6$ to about $2.0 \times 10^6$ platelets in about 6 hours.

13. The composition of claim 8, wherein the platelets produced from the plurality of megakaryocytes bind PAC-1.

14. The composition of claim 13, wherein the platelets produced from the plurality of megakaryocytes bind PAC-1 following stimulation with thrombin, ADP and/or epinephrine.

15. The composition of claim 1, wherein the porous silk membrane is tubular.

16. The composition of claim 1, wherein the pores in the silk membrane have a diameter between about 1-50 μm, inclusive.

17. The composition of claim 1, wherein the porous silk membrane is about 50-70 μm thick, inclusive.

18. The composition of claim 1, wherein the pores of the three dimensional silk matrix have a diameter of between about 300 and 500 μm, inclusive.

19. The composition of claim 1, wherein the porous silk membrane is made via gel spinning.

20. The composition of claim 1, wherein the plurality of megakaryocytes comprises at least $2.0 \times 10^5$ megakaryocytes.

21. A method of forming the composition of claim 1 comprising:
   providing a silk membrane between about 2 μm and 100 μm thick, inclusive;
   contacting the silk membrane with a porogen to form a porous silk membrane comprising at least one silk wall defining a lumen;
   associating the porous silk membrane with stromal derived factor-1α and at least one functionalizing agent selected from the group consisting of fibronectin, collagen type IV, collagen type VI, von Willebrand factor, laminin, and fibrinogen; and
   forming a three dimensional silk matrix comprising pores, wherein the pores are interconnected and the pores have a diameter of between about 5 and 500 μm, inclusive, and
   wherein the three dimensional silk matrix is formed around at least a portion of the porous silk membrane, thereby forming a composition adapted to receive a plurality of megakaryocytes that, in use, produce differentiated and functional platelets.

22. A method of producing platelets, the method comprising:
   providing a silk membrane between about 2 μm and 100 μm thick, inclusive;
   contacting the silk membrane with a porogen to form a porous silk membrane comprising at least one silk wall defining a lumen;
   associating the porous silk membrane with stromal derived factor-1α and at least one functionalizing agent selected from the group consisting of fibronectin, collagen type IV, collagen type VI, von Willebrand factor, laminin, and fibrinogen;

forming a three dimensional silk matrix comprising pores, wherein the pores are interconnected and the pores have a diameter of between about 5 and 500 μm, inclusive, wherein the three dimensional silk matrix is formed around at least a portion of the porous silk membrane;

introducing a plurality of megakaryocytes to the three dimensional silk matrix such that the plurality of megakaryocytes are located at least partially within the porous silk membrane; and stimulating the plurality of megakaryocytes to produce differentiated and functional platelets.

23. A method of producing platelets, the method comprising activating a system comprising the composition of claim 1, the composition also comprising megakaryocytes, wherein at least about $0.8 \times 10^6$ to about $2.0 \times 10^6$ platelets are produced by the system in 6 hours.

* * * * *

UNITED STATES PATENT AND TRADEMARK OFFICE
CERTIFICATE OF CORRECTION

PATENT NO. : 11,802,270 B2  
APPLICATION NO. : 15/501607  
DATED : October 31, 2023  
INVENTOR(S) : Balduini et al.

Page 1 of 1

It is certified that error appears in the above-identified patent and that said Letters Patent is hereby corrected as shown below:

In the Specification

In Column 8, Line 63, delete "vents." and insert --events.-- therefor

In Column 10, Line 58, after ""determining"", insert --.--

In Column 12, Line 5, delete "factor-1a," and insert --factor-1α,-- therefor

In Column 16, Line 36, delete "µg/m1)." and insert --µg/ml).-- therefor

In Column 21, Line 49, after "surface", insert --.--

In Column 23, Line 5, after "Germany)", insert --.--

In Column 28, Lines 39-40, delete "anti-β-tubulin" and insert --anti-β1-tubulin-- therefor In Column 30, Line 53, delete "SDF-la." and insert --SDF-1α.-- therefor In Column 34, Line 2, delete "assess" and insert --asses-- therefor In Column 34, Line 39, delete "90±2" and insert --9±2-- therefor In Column 35, Line 32, after "12a)", insert --.--

In Column 36, Line 28, after "14a)", insert --.--

Signed and Sealed this  
Twenty-seventh Day of February, 2024

*Katherine Kelly Vidal*  
Katherine Kelly Vidal  
*Director of the United States Patent and Trademark Office*